(12) United States Patent
Eggenweiler et al.

(10) Patent No.: US 7,135,471 B2
(45) Date of Patent: Nov. 14, 2006

(54) ARYL OXIMES

(75) Inventors: Hans-Michael Eggenweiler, Darmstadt (DE); Norbert Beier, Reinheim (DE); Pierre Schelling, Mühltal (DE); Michael Wolf, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 1 day.

(21) Appl. No.: 10/517,438

(22) PCT Filed: May 16, 2003

(86) PCT No.: PCT/EP03/05173

§ 371 (c)(1),
(2), (4) Date: Dec. 10, 2004

(87) PCT Pub. No.: WO03/104205

PCT Pub. Date: Dec. 18, 2003

(65) Prior Publication Data

US 2005/0209240 A1    Sep. 22, 2005

(30) Foreign Application Priority Data

Jun. 10, 2002    (DE) ................. 102 25 574

(51) Int. Cl.
- C07D 403/12    (2006.01)
- C07D 237/04    (2006.01)
- A61K 31/501   (2006.01)
- A61K 31/50    (2006.01)

(52) U.S. Cl. .............. 514/241; 514/247; 514/248; 514/249; 514/252.03; 514/252.04; 514/252.05; 544/182; 544/215; 544/235; 544/237; 544/224; 544/238; 260/570

(58) Field of Classification Search ................ 544/224, 544/238, 182, 215, 235, 237; 514/247, 241, 514/248, 249, 252.02, 252.03, 252.04, 252.05; 206/570

See application file for complete search history.

(56) References Cited

FOREIGN PATENT DOCUMENTS

| WO | WO 98/06704 | 2/1998 |
| WO | WO 99/65880 | 12/1999 |

*Primary Examiner*—Kahsay Habte
(74) *Attorney, Agent, or Firm*—Millen, White, Zelano & Branigan, P.C.

(57) ABSTRACT

Aryl oxime derivatives of the formula (I), in which $R^1$, $R^2$, $R^3$, X and B are as defined in claim 1, act as phosphodiesterase IV inhibitors and can be employed for the treatment of osteoporosis, tumours, cachexia, atherosclerosis, rheumatoid arthritis, multiple sclerosis, diabetes mellitus, inflammatory processes, allergies, asthma, autoimmune diseases, myocardial diseases and AIDS (I)

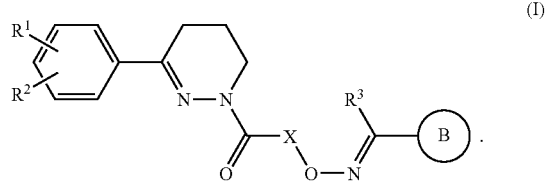

15 Claims, No Drawings

ARYL OXIMES

The invention relates to compounds of the formula I

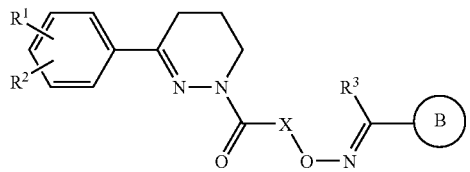

in which
R¹, R² are each, independently of one another, H, OH, OR⁸, —SR⁸, —SOR⁸, —SO₂R⁸ or Hal,
R¹ and R² together are alternatively —OCH₂O— or —OCH₂CH₂O—,
R³ is H, A"R⁷, COA"R⁷, COOA"R⁷, CONH₂, CONHA"R⁷, CON(A"R⁷)(A'"R⁷), CONR¹⁰Het, NH₂, NHA"R⁷, N(A"R⁷)(A'"R⁷), NCOA"R⁷ or NCOOA"R⁷,
B is an aromatic isocyclic or heterocyclic radical, which may be unsubstituted or monosubstituted, disubstituted or trisubstituted by R⁴, R⁵ and/or R⁶,
X is alkylene having 1–10 carbon atoms or alkenylene having 2–8 carbon atoms,
in which one, two or three CH₂ groups may be replaced by O, S, SO, SO₂, NH or NA"R⁷,
1–7 H atoms may be replaced by F and/or Cl,
R⁴, R⁵, R⁶ are each, independently of one another, H, A"R⁷, OH, OA"R⁷, NO₂, NH₂, NHA"R⁷, N(A"R⁷)(A'"R⁷), NHCOA"R⁷, NHCOOA"R⁷, NHCONH₂, NHCONHA"R⁷, NHCON(A"R⁷)(A'"R⁷), Hal, COOH, COOA"R⁷, CONH₂, CONHA"R⁷, CON(A"R⁷)(A'"R⁷),

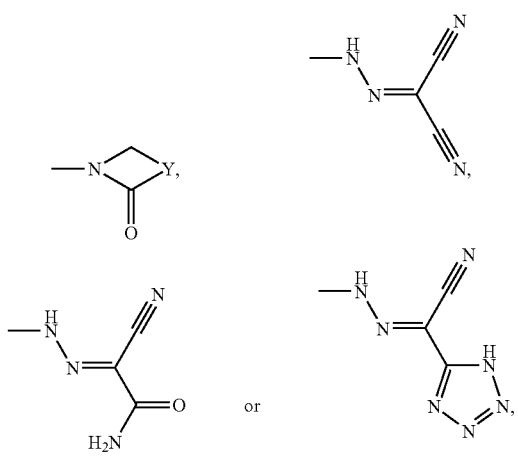

R⁷ is H, COOH, COOA, CONH₂, CONHA, CONAA', NH₂, NHA, NAA', NCOA, NCOOA, OH or OA,
R⁸ is A, cycloalkyl having 3–7 carbon atoms, alkylenecycloalkyl having 4–8 carbon atoms or alkenyl having 2–8 carbon atoms,
R⁹ is alkyl having 1–10 carbon atoms, cycloalkyl having 3–7 carbon atoms, alkylenecycloalkyl having 4–8 carbon atoms or alkenyl having 2–8 carbon atoms,
in which one, two or three CH₂ groups may be replaced by O, S, SO, SO₂, NH, NMe, NEt and/or by —CH=CH— groups, 1–7 H atoms may be replaced by F and/or Cl, and/or 1 H atom may be replaced by R⁷,
Y is alkylene having 1–10 carbon atoms or alkenylene having 2–8 carbon atoms,
in which one, two or three CH₂ groups may be replaced by O, S, SO, SO₂, NH or NR⁹ and/or
1–7 H atoms may be replaced by F and/or Cl,
A, A' are each, independently of one another, alkyl having 1–10 carbon atoms or alkenyl having 2–8 carbon atoms,
in which one, two or three CH₂ groups may be replaced by O, S, SO, SO₂, NH or NR⁹ and/or
1–7 H atoms may be replaced by F and/or Cl, or
aryl or Het,
A and A' together are alternatively an alkylene chain having 2–7 carbon atoms, in which one, two or three CH₂ groups may be replaced by O, S, SO, SO₂, NH, NR⁹, NCOR⁹ or NCOOR⁹,
A", A'" are each, independently of one another,
absent, alkylene having 1–10 carbon atoms, alkenylene having 2–8 carbon atoms or cycloalkylene having 3–7 carbon atoms,
in which one, two or three CH₂ groups may be replaced by O, S, SO, SO₂, NH or NR⁹ and/or
1–7 H atoms may be replaced by F and/or Cl,
A" and A'" together are alternatively an alkylene chain having 2–7 carbon atoms, in which one, two or three CH₂ groups may be replaced by O, S, SO, SO₂, NH, NR⁹, NCOR⁹ or NCOOR⁹,
aryl is phenyl, naphthyl, fluorenyl or biphenyl, each of which is unsubstituted or monosubstituted, disubstituted or trisubstituted by Hal, R¹¹, OR¹⁰, N(R¹⁰)₂, NO₂, CN, COOR¹⁰, CON(R¹⁰)₂, NR¹⁰COR¹⁰, NR¹⁰CON(R¹⁰)₂, NR¹⁰SO₂A, COR¹⁰, SO₂N(R¹⁰)₂, S(O)ₘR¹¹,
R¹⁰ is H or alkyl having 1–6 carbon atoms,
R¹¹ is alkyl having 1–6 carbon atoms,
Het is a monocyclic or bicyclic saturated, unsaturated or aromatic heterocyclic ring having 1 to 2 N, O and/or S atoms, which may be unsubstituted or monosubstituted or disubstituted by carbonyl oxygen, Hal, R¹¹, OR¹⁰, N(R¹⁰)₂, NO₂, CN, COOR¹⁰, CON(R¹⁰)₂, NR¹⁰COR¹⁰, NR¹⁰CON(R¹⁰)₂, NR¹⁰SO₂R¹¹, COR¹⁰, SO₂NR¹⁰ and/or S(O)ₘR¹¹,
Hal is F, Cl, Br or I,
m is 0, 1 or 2, and pharmaceutically usable derivatives, solvates, stereoisomers and E/Z isomers thereof, including mixtures thereof in all ratios.

1-Benzoyltetrahydropyridazines as progesterone receptor ligands are described, for example, in J. Med. Chem. 38, 4878 (1995).

Further arylalkanoylpyridazines are disclosed, for example, in EP 0 922 036, EP 1 124 809 or WO 01/04099.

The invention had the object of finding novel compounds having valuable properties, in particular those which can be used for the preparation of medicaments.

It has been found that the compounds of the formula I and salts and solvates thereof have very valuable pharmacological properties and are well tolerated.

The compounds of the formula I exhibit selective phosphodiesterase IV inhibition which is associated with an intracellular increase of cAMP (N. Sommer et al., Nature Medicine, 1, 244–248 (1995)). The PDE IV inhibition can be detected, for example, analogously to C. W. Davis in Biochim. Biophys. Acta 797, 354–362 (1984).

The affinity of the compounds according to the invention for phosphodiesterase IV is determined by measuring their IC$_{50}$ values (concentration of the inhibitor that is required in order to achieve 50% inhibition of the enzyme activity).

The compounds according to the invention can be employed for the treatment of asthmatic diseases. The anti-asthmatic action of the PDE IV inhibitors is described, for example, by T. J. Torphy et al. in Thorax, 46, 512–523 (1991), and can be determined, for example, by the method of T. Olsson, Acta allergologica 26, 438–447 (1971).

Since cAMP inhibits osteoclastic cells and stimulates osteogenetic cells (S. Kasugai et al., M 681, and K. Miyamoto, M 682, in Abstracts of the American Society for Bone and Mineral Research, 18$^{th}$ Annual Meeting, 1996), the compounds according to the invention can be employed for the treatment of osteoporosis.

In addition, the compounds exhibit an antagonistic action to the production of TNF (tumour necrosis factor) and are therefore suitable for the treatment of allergic and inflammatory diseases, autoimmune diseases, such as, for example, rheumatoid arthritis, multiple sclerosis, Crohn's disease, diabetes mellitus or ulcerative colitis, transplant rejection reactions, cachexia and sepsis.

The anti-inflammatory action of the substances according to the invention and their effectiveness for the treatment of, for example, autoimmune disorders, such as multiple sclerosis or rheumatoid arthritis, can be determined analogously to the methods of N. Sommer et al., Nature Medicine 1, 244–248 (1995), or L. Sekut et al., Clin. Exp. Immunol. 100, 126–132 (1995).

The compounds can be employed for the treatment of cachexia. The anti-cachectic action can be tested in TNF-dependent models of cachexia (P. Costelli et al., J. Clin. Invest. 95, 2367ff. (1995); J. M. Argiles et al., Med. Res. Rev. 17, 477 ff. (1997)).

PDE IV inhibitors can also inhibit the growth of tumour cells and are therefore suitable for tumour therapy (D. Marko et al., Cell Biochem. Biophys. 28, 75 ff. (1998)). The action of PDE IV inhibitors in the treatment of tumours is described, for example, in WO 95 35 281, WO 95 17 399 or WO 9600215.

PDE IV inhibitors can prevent mortality in models of sepsis and are therefore suitable for the therapy of sepsis (W. Fischer et al., Biochem. Pharmacol. 45, 2399ff. (1993)).

They can furthermore be employed for the treatment of memory disorders, atherosclerosis, atopic dermatitis and AIDS.

The action of PDE IV inhibitors in the treatment of asthma, inflammatory diseases, diabetes mellitus, atopic dermatitis, psoriasis, AIDS, cachexia, tumour growth or tumour metastases is described, for example, in EP 77 92 91.

The compounds of the formula I can be employed as medicament active ingredients in human and veterinary medicine. They can furthermore be employed as intermediates for the preparation of further medicament active ingredients.

Furthermore, the invention relates to the use of type 4 phosphodiesterase inhibitors (PDE IV inhibitors) of the formula I for the treatment of diseases and relates to combinations of compounds of the formula I with other medicaments.

Reference is made to WO 01/57025 which discloses special pyrimidine derivatives as PDE IV inhibitors, the use thereof for the treatment of diseases and combinations with other medicaments.

Accordingly, the invention relates in particular to the use of compounds of the formula I and physiologically acceptable salts and solvates thereof for the preparation of a medicament for the treatment of a patient suffering from a disease or condition mediated by the PDE IV isozyme in its role of regulating the activation and degranulation of human eosinophils.

WO 01/57025 discloses various in-vitro assays and animal model experiments, which are capable of providing data sufficient to define and demonstrate therapeutic utility of compounds of the formula I.

Compounds of the formula I inhibit the PDE IV isozyme and are therefore suitable for a wide range of therapeutic applications, because of the essential role which the PDE IV family of isozymes plays in the physiology of all mammals. The enzymatic role performed by the PDE IV isozymes is the intracellular hydrolysis of adenosine 3',5'-monophosphate (cAMP) within pro-inflammatory leukocytes. cAMP, in turn, is responsible for mediating the effects of numerous hormones in the body, and as a consequence, PDE IV inhibition plays a significant role in a variety of physiological processes. There is extensive literature in the art describing the effects of PDE inhibitors on various inflammatory cell responses, which in addition to cAMP elevation, also include inhibition of superoxide production, degranulation, chemotaxis and tumour necrosis factor (TNF) release in eosinophils, neutrophils and monocytes.

The invention therefore relates to the compounds of the formula I and to a process for the preparation of compounds of the formula I and salts and solvates thereof, characterised in that a) a compound of the formula II

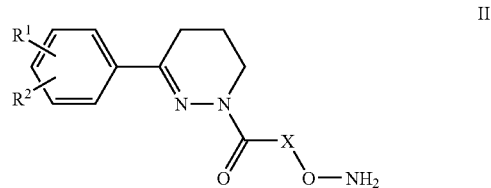

in which

X, R$^1$ and R$^2$ are as defined in claim 1, is reacted with a compound of the formula III

in which

R$^3$ and B are as defined in claim 1, with the proviso that any further OH and/or amino group present is protected, and subsequently, if desired, a protecting group is removed, or b) a compound of the formula IV

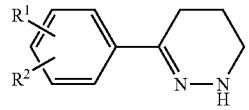

in which $R^1$ and $R^2$ are as defined in claim 1, is reacted with a compound of the formula V

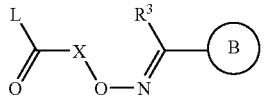

in which

L is Cl, Br, I or a free or reactively functionally modified OH group, and $R^3$, X and B are as defined in claim 1, with the proviso that any further OH and/or amino group present is protected, and subsequently, if desired, a protecting group is removed, or c) a compound of the formula VI

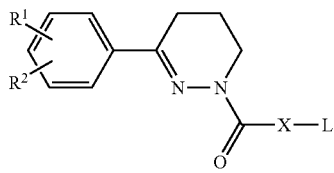

in which

X, $R^1$ and $R^2$ are as defined in claim 1, and

L is Cl, Br, I or a free or reactively functionally modified OH group, is reacted with a compound of the formula VII

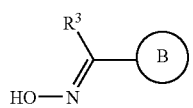

in which $R^3$ and B are as defined in claim 1, with the proviso that any further OH and/or amino group present is protected, and subsequently, if desired, a protecting group is removed, or d) one or more radicals $R^1$, $R^2$, $R^3$ and/or B in a compound of the formula I are converted into one or more other radicals $R^1$, $R^2$, $R^3$ and/or B by i) cleaving an ether or ester,
ii) alkylating or acylating an OH function,
iii) reductively alkylating an amino group,
iv) reacting an amino group with malononitrile,
v) converting a cyano group into a tetrazole group, and/or in that a basic compound of the formula I is converted into one of its salts by treatment with an acid.

In addition, the invention relates to the optically active forms (stereoisomers), the E/Z isomers, the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, monohydrates, dihydrates or alcoholates.

The term pharmaceutically usable derivatives is taken to mean, for example, the salts of the compounds according to the invention and so-called prodrug compounds.

The term prodrug derivatives is taken to mean, for example, compounds of the formula I which have been modified, for example, with alkyl or acyl groups, sugars or oligopeptides and which are rapidly cleaved in the organism and thus release the active ingredients according to the invention.

These also include biodegradable polymer derivatives of the compounds according to the invention, as described, for example, in Int. J. Pharm. 115, 61–67 (1995).

The following abbreviations are used below:

| | |
|---|---|
| Ac | acetyl |
| BOC | tert-butoxycarbonyl |
| CBZ or Z | benzyloxycarbonyl |
| DCCI | dicyclohexylcarbodiimide |
| DCM | dichloromethane |
| DMF | dimethylformamide |
| EA | ethyl acetate |
| EDCI | N-ethyl-N,N'-(dimethylaminopropyl)carbodiimide |
| Et | ethyl |
| Fmoc | 9-fluorenylmethoxycarbonyl |
| HOBt | 1-hydroxybenzotriazole |
| Me | methyl |
| MBHA | 4-methylbenzhydrylamine |
| Mtr | 4-methoxy-2,3,6-trimethylphenylsulfonyl |
| HONSu | N-hydroxysuccinimide |
| OBut | tert-butyl ester |
| Oct | octanoyl |
| OMe | methyl ester |
| OEt | ethyl ester |
| POA | phenoxyacetyl |
| TFA | trifluoroacetic acid |
| Trt | trityl (triphenylmethyl). |

The meanings of all radicals which occur more than once are in each case independent of one another.

Above and below, the radicals $R^1$, $R^2$, $R^3$, X, B and L are as defined in the formulae I, II, III, IV, V, VI and VII, unless expressly stated otherwise.

Alkyl having 1–10 carbon atoms is alkyl having 1, 2, 3, 4, 5, 6, 7, 8, 9 or 10 carbon atoms, is branched or unbranched, and is preferably alkyl having 1, 2, 3, 4, 5 or 6 carbon atoms and is, for example, methyl, ethyl, trifluoromethyl, pentafluoroethyl or propyl, furthermore preferably isopropyl, butyl, isobutyl, sec-butyl or tert-butyl, but also n-pentyl, neopentyl, isopentyl or n-hexyl. Particular preference is given to methyl, ethyl, trifluoromethyl, propyl, isopropyl, butyl, n-pentyl, n-hexyl or n-decyl.

Cycloalkyl preferably has 3–7 carbon atoms and is preferably cyclopropyl or cyclobutyl, furthermore preferably cyclopentyl or cyclohexyl, furthermore also cycloheptyl; particular preference is given to cyclopentyl.

Alkenyl is preferably vinyl, allyl, 2- or 3-butenyl, isobutenyl or sec-butenyl; preference is furthermore given to 4-pentenyl, isopentenyl or 5-hexenyl.

Alkylene is preferably unbranched and is preferably methylene or ethylene, furthermore preferably propylene or butylene.

Alkylenecycloalkyl is, for example, cyclohexylmethyl or cyclopentylethyl.

Alkyl having 1–6 carbon atoms is alkyl having 1, 2, 3, 4, 5 or 6 carbon atoms, is branched or unbranched, and is, for example, methyl, ethyl, trifluoromethyl, pentafluoroethyl or propyl, furthermore preferably isopropyl, butyl, isobutyl, sec-butyl or tert-butyl, but also n-pentyl, neopentyl, isopentyl or n-hexyl. Particular preference is given to methyl, ethyl, trifluoromethyl, propyl, isopropyl, butyl, n-pentyl or n-hexyl.

Hal is preferably F, Cl or Br, furthermore also I.

The radicals $R^1$ and $R^2$ may be identical or different and are preferably in the 3- or 4-position of the phenyl ring. They are, for example, independently of one another, H, hydroxyl, —S—$CH_3$, —SO—$CH_3$, —$SO_2CH_3$, F, Cl, Br or I or together are methylenedioxy. However, they are preferably each methyl, ethyl, propyl, methoxy, ethoxy, propoxy, isopropoxy, benzyloxy, or alternatively fluoro-, difluoro- or trifluoromethoxy or 1-fluoro-, 2-fluoro-, 1,2-difluoro-, 2,2-difluoro-, 1,2,2-trifluoro- or 2,2,2-trifluoroethoxy.

In a further embodiment, $R^1$ and $R^2$ are each, independently of one another, alkoxy having 1, 2, 3, 4, 5 or 6 carbon atoms.

Alkoxy is, for example, methoxy, ethoxy, propoxy, isopropoxy, butoxy, pentoxy or hexoxy.

In a further embodiment, $R^1$ and $R^2$ are each, independently of one another, alkoxy having 1, 2, 3, 4, 5 or 6 carbon atoms.

Alkoxy is, for example, methoxy, ethoxy, propoxy, isopropoxy, butoxy, pentoxy or hexoxy.

$R^1$ is particularly preferably ethoxy, benzyloxy, F, propoxy or isopropoxy, furthermore difluoromethoxy or cycloalkoxy, for example cyclopentoxy. $R^1$ is very particularly preferably 4-methoxy.

$R^2$ is particularly preferably methoxy, ethoxy, 3-propoxy, F or ethyl, furthermore difluoromethoxy or cycloalkoxy, for example cyclopentoxy. $R^2$ is very particularly preferably 3-ethoxy or 3-propoxy.

$R^3$ is preferably H, A"$R^7$, COA"$R^7$, CON(A"'$R^7$)(A"'$R^7$) or CO—$NR^{10}$-Het. $R^3$ is very particularly preferably, for example, H, COOH, CO—$CH_2$—NAA', CO—$CH_2$—$CH_2$—NAA', CO—$CH_2$—NHA', CO—$CH_2$—$CH_2$—NHA', 1-methylpiperazin-4-ylcarbonyl, 1-methylpiperidin-4-yl-N-methylaminocarbonyl.

X is preferably methylene, ethylene, propylene or butylene, very particularly preferably methylene.

B is preferably phenyl, pyridyl, pyridyl N-oxide, thienyl, furyl, pyrrolyl, pyridazinyl, pyrimidinyl, pyrazinyl, triazinyl, isoxazolinyl, oxazolinyl, thiazolinyl, pyrazolinyl, imidazolinyl, naphthyl, quinolinyl, isoquinolinyl, cinnolinyl, phthalazinyl, quinazolinyl or quinoxalinyl, each of which is unsubstituted or may be monosubstituted, disubstituted or trisubstituted by $R^4$, $R^5$ and/or $R^6$.

In a further preferred embodiment, B is phenyl, pyridyl, pyridyl N-oxide, thienyl, furyl, pyrrolyl, pyridazinyl, pyrimidinyl, pyrazinyl, triazinyl, isoxazolinyl, oxazolinyl, thiazolinyl, pyrazolinyl, imidazolinyl, naphthyl, quinolinyl, isoquinolinyl, cinnolinyl, phthalazinyl, quinazolinyl or quinoxalinyl, each of which is unsubstituted or may be monosubstituted, disubstituted or trisubstituted by OH, OA, $NO_2$, $NH_2$, NAA',

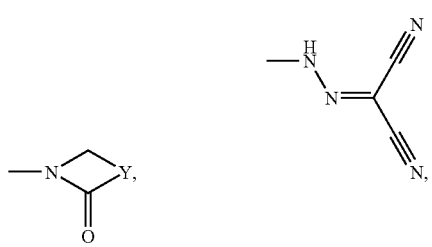

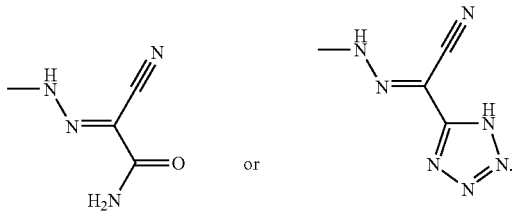

In a further preferred embodiment, B is phenyl which is unsubstituted or monosubstituted by $OR^{10}$, $NO_2$ or

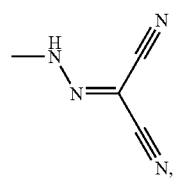

or unsubstituted pyridyl or pyridyl N-oxide.

$R^4$ is preferably H, $OR^{10}$, $NO_2$ or

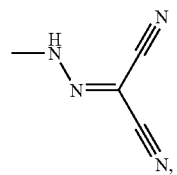

furthermore preferably $NH_2$ or NHCOOA"$R^7$.

$R^5$ and $R^6$ are preferably H.

$R^7$ is preferably H, COOH, NHA or NAA'.

$R^8$ is preferably $R^{11}$, cycloalkyl having 3–7 carbon atoms or alkylenecycloalkyl having 4–8 carbon atoms.

$R^9$ is preferably alkyl having 1–10 carbon atoms, very particularly preferably alkyl having 1–6 carbon atoms.

Y is preferably methylene, ethylene, propylene or butylene.

A, A' are preferably each, independently of one another, alkyl having 1–10 carbon atoms, in which 1–7 H atoms may be replaced by F and/or Cl, or are each, independently of one another, aryl or Het.

A", A"' are preferably each, independently of one another: absent or alkylene having 1–10 carbon atoms, in which one $CH_2$ group may be replaced by NH or $NR^9$.

A", A"' are preferably together alternatively an alkylene chain having 2–7 carbon atoms, in which one $CH_2$ group may be replaced by NH or $NR^9$.

Aryl is, for example, unsubstituted phenyl, naphthyl, fluorenyl or biphenyl, furthermore preferably phenyl, naphthyl, fluorenyl or biphenyl, each of which is monosubstituted, disubstituted or trisubstituted, for example, by methyl, ethyl, propyl, butyl, fluorine, chlorine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, sulfonamido, methylsulfonamido, ethylsulfonamido, propylsulfonamido, butylsulfonamido, dimethylsulfonamido, carboxyl, methoxycarbonyl, ethoxycarbonyl or aminocarbonyl.

Het is, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4-or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benz-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or completely hydrogenated.

Het can thus also be, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-, -pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or alternatively 3,4-dihydro-2H-1,5-benzodioxepin-6- or -7-yl, furthermore preferably 2,3-dihydrobenzofuranyl or 2,3-dihydro-2-oxofuranyl.

In a further embodiment, Het is particularly preferably unsubstituted pyridyl, pyridyl N-oxide, thienyl, furyl, pyrrolyl, pyridazinyl, pyrimidinyl, pyrazinyl, triazinyl, isoxazolinyl, oxazolinyl, thiazolinyl, pyrazolinyl, imidazolinyl, naphthyl, quinolinyl, isoquinolinyl, cinnolinyl, phthalazinyl, quinazolinyl or quinoxalinyl, very particularly preferably pyridyl.

In a further preferred embodiment, Het is a monocyclic saturated or unsaturated heterocyclic ring having 1 to 2 N and/or O atoms, which may be monosubstituted or disubstituted by carbonyl oxygen, OH or OA. Het therein is particularly preferably, for example, 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-hydroxy-6-oxopiperazin-1-yl, 2-methoxy-6-oxopiperazin-1-yl, 2-azabicyclo[2.2.2]-octan-3-on-2-yl, very particularly preferably 2-oxopiperidin-1-yl.

In a further embodiment, Het is very particularly preferably a monocyclic saturated heterocyclic radical having 1 to 2 N atoms, which may be mono-substituted or disubstituted by alkyl having 1–6 carbon atoms.

Accordingly, the compound relates, in particular, to the compounds of the formula I in which at least one of the said radicals has one of the preferred meanings given above. Some preferred groups of compounds may be expressed by the following sub-formulae Ia to Ik, which conform to the formula I and in which the radicals not denoted in greater detail are as defined for the formula I, but in which in Ia
$R^1$, $R^2$ are each, independently of one another, alkoxy having 1, 2, 3, 4, 5 or 6 carbon atoms;

in Ib
$R^1$, $R^2$ are each, independently of one another, H, methoxy, ethoxy, benzyloxy, propoxy, isopropoxy, difluoromethoxy, F, Cl, cyclopentyloxy, cyclohexyloxy or cycloheptyloxy;

in Ic
$R^1$, $R^2$ are each, independently of one another, methoxy, ethoxy, propoxy, isopropoxy, cyclopentyloxy or F;

in Id
$R^1$ is 4-methoxy,
$R^2$ is 3-ethoxy or 3-propoxy;

in Ie
$R^3$ is H, A"$R^7$, COA"$R^7$, CON(A"$R^7$)(A'"$R^7$) or CO—NR$^{10}$-Het;

in If
X is methylene, ethylene, propylene or butylene;

in Ig
B is phenyl, pyridyl, pyridyl N-oxide, thienyl, furyl, pyrrolyl, pyridazinyl, pyrimidinyl, pyrazinyl, triazinyl, isoxazolinyl, oxazolinyl, thiazolinyl, pyrazolinyl, imidazolinyl, naphthyl, quinolinyl, isoquinolinyl, cinnolinyl, phthalazinyl, quinazolinyl or quinoxalinyl, each of which is unsubstituted or may be monosubstituted, disubstituted or trisubstituted by $R^4$, $R^5$ and/or $R^6$;

in Ih
B is phenyl, pyridyl, pyridyl N-oxide, thienyl, furyl, pyrrolyl, pyridazinyl, pyrimidinyl, pyrazinyl, triazinyl, isoxazolinyl, oxazolinyl, thiazolinyl, pyrazolinyl, imidazolinyl, naphthyl, quinolinyl, isoquinolinyl, cinnolinyl, phthalazinyl, quinazolinyl or quinoxalinyl, each of which is unsubstituted or may be monosubstituted, disubstituted or trisubstituted by OH, OA, NO$_2$, NH$_2$, NAA',

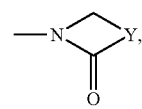

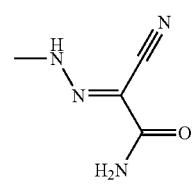 or 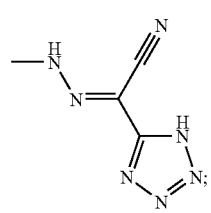

in Ii

B is phenyl which is unsubstituted or monosubstituted by $OR^{10}$, $NO_2$ or

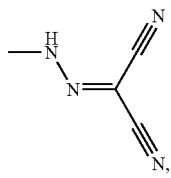

or unsubstituted pyridyl or pyridyl N-oxide;

in Ij $R^1$, $R^2$ are each, independently of one another, alkoxy having 1, 2, 3, 4, 5 or 6 carbon atoms, X is methylene, ethylene, propylene or butylene, $R^3$ is H, A"$R^7$, COA"$R^7$, CON(A"$R^7$)(A'''$R^7$) or CO—$NR^{10}$-Het, A", A''' are each, independently of one another, absent or alkylene having 1–10 carbon atoms, in which one $CH_2$ group may be replaced by NH or $NR^9$, A", A''' together are alternatively an alkylene chain having 2–7 carbon atoms, in which one $CH_2$ group may be replaced by NH or $NR^9$, B is phenyl which is unsubstituted or monosubstituted by $OR^{10}$, $NO_2$,

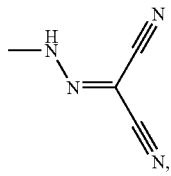

$NH_2$ or NHCOOA"$R^7$, or unsubstituted pyridyl or pyridyl N-oxide, $R^7$ is H, COOH, NHA or NAA', $R^9$ is alkyl having 1–6 carbon atoms, $R^{10}$ is H or alkyl having 1–6 carbon atoms, A, A' are each, independently of one another, alkyl having 1–10 carbon atoms, in which 1–7 H atoms may be replaced by F and/or Cl, Het is a monocyclic saturated heterocyclic radical having 1 to 2 N atoms, which may be monosubstituted or disubstituted by alkyl having 1–6 carbon atoms;

in Ik $R^1$, $R^2$ are each, independently of one another, alkoxy having 1, 2, 3, 4, 5 or 6 carbon atoms, X is methylene, ethylene, propylene or butylene, $R^3$ is H, A"$R^7$, COA"$R^7$, CON(A"$R^7$)(A'''$R^7$) or CO—$NR^{10}$-Het, A", A''' are each, independently of one another, absent or alkylene having 1–10 carbon atoms, in which one $CH_2$ group may be replaced by NH or $NR^9$, A", A''' together are alternatively an alkylene chain having 2–7 carbon atoms, in which one $CH_2$ group may be replaced by NH or $NR^9$, B is phenyl which is unsubstituted or monosubstituted by $OR^{10}$, $NO_2$,

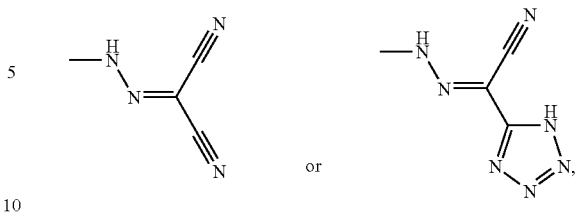

$NH_2$ or NHCOOA"$R^7$, or unsubstituted pyridyl or pyridyl N-oxide, $R^7$ is H, COOH, NHA or NAA', $R^9$ is alkyl having 1–6 carbon atoms, $R^{10}$ is H or alkyl having 1–6 carbon atoms, A, A' are each, independently of one another, alkyl having 1–10 carbon atoms, in which 1–7 H atoms may be replaced by F and/or Cl, Het is a monocyclic saturated heterocyclic radical having 1 to 2 N atoms, which may be monosubstituted or disubstituted by alkyl having 1–6 carbon atoms;

and pharmaceutically usable derivatives, solvates, stereoisomers and E/Z isomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

In the compounds of the formulae II, III, IV, V, VI and VII, $R^1$, $R^2$, $R^3$, X and B have the meanings indicated, in particular the preferred meanings indicated.

Some of the starting materials of the formula II are known. If they are not known, they can be prepared by methods known per se.

Some of the starting materials of the formula III are known. If they are not known, they can be prepared by methods known per se.

If desired, the starting materials can also be formed in situ by not isolating them from the reaction mixture, but instead immediately converting them further into the compounds of the formula I.

On the other hand, it is possible to carry out the reaction stepwise.

The compounds of the formula I can preferably be obtained by reacting compounds of the formula II with compounds of the formula III.

Compounds of the formula I are preferably prepared, for example, in accordance with the following reaction scheme:

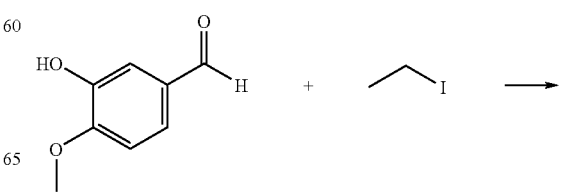

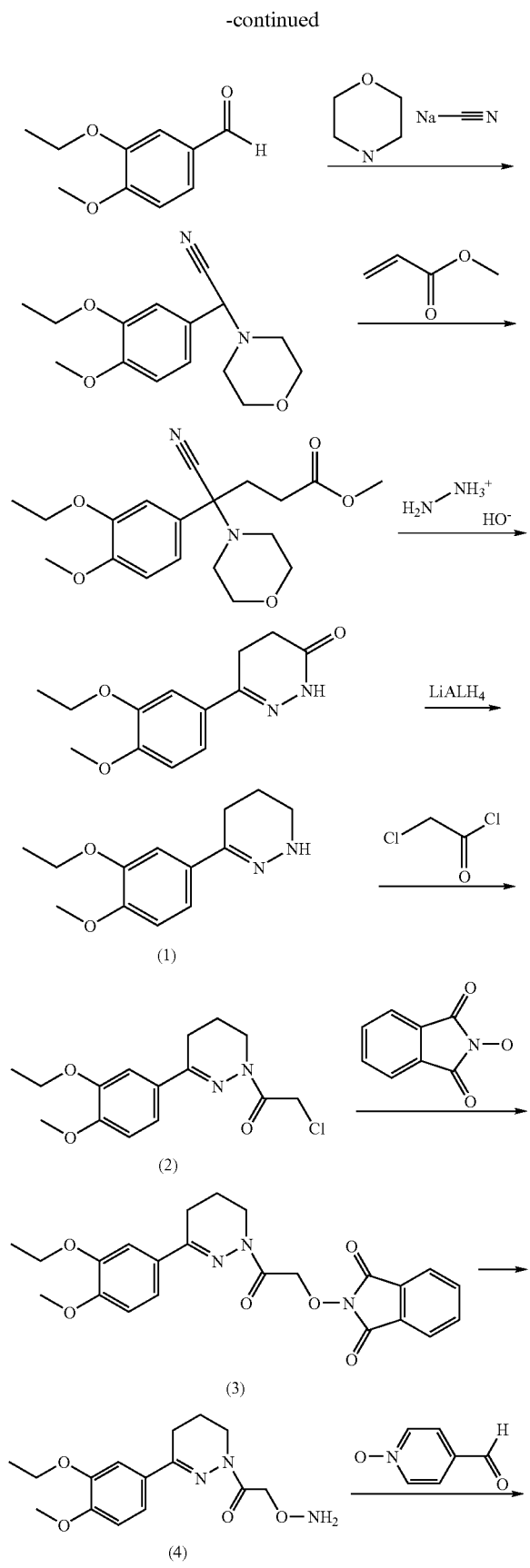

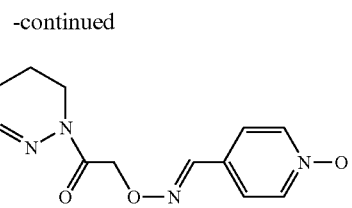

In detail, the reaction of the compounds of the formula II with the compounds of the formula III is carried out in the presence or absence of an inert solvent at temperatures between approximately −20 and approximately 150°, preferably between 20 and 100°.

Examples of suitable inert solvents are hydrocarbons, such as hexane, petroleum ether, benzene, toluene or xylene; chlorinated hydrocarbons, such as trichloroethylene, 1,2-dichloroethane, tertachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Compounds of the formula I can furthermore be obtained by reacting compounds of the formula IV with compounds of the formula V.

Some of the starting materials of the formula IV are known. If they are not known, they can be prepared by methods known per se.

Some of the starting materials of the formula V are known. If they are not known, they can be prepared by methods known per se.

In the compounds of the formula V, L is preferably Cl, Br, I or a free or reactively modified OH group, such as, for example, an activated ester, an imidazolide or alkylsulfonyloxy having 1–6 carbon atoms (preferably methylsulfonyloxy or trifluoromethylsulfonyloxy) or arylsulfonyloxy having 6–10 carbon atoms (preferably phenyl- or p-tolylsulfonyloxy). Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example by addition of HOBt or N-hydroxysuccinimide.

The reaction is carried out at temperatures and in solvents as described for the reaction of compounds of the formula II with those of the formula III.

Compounds of the formula I can furthermore be obtained by reacting compounds of the formula VI with compounds of the formula VII.

Some of the starting materials of the formula VI are known. If they are not known, they can be prepared by methods known per se.

Some of the starting materials of the formula VII are known. If they are not known, they can be prepared by methods known per se.

In the compounds of the formula VI, L is preferably Cl, Br, I or a free or reactively modified OH group, such as, for example, an activated ester, an imidazolide or alkylsulfonyloxy having 1–6 carbon atoms (preferably methylsulfonyloxy or trifluoromethylsulfonyloxy) or arylsulfonyloxy having 6–10 carbon atoms (preferably phenyl- or p-tolylsulfonyloxy).

The reaction is carried out at temperatures and in solvents as described for the reaction of compounds of the formula II with those of the formula III.

Compounds of the formula I can furthermore be obtained by liberating compounds of the formula I from one of their functional derivatives by treatment with a solvolysing or hydrogenolysing agent.

Preferred starting materials for the solvolysis or hydrogenolysis are those which conform to the formula I, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' is an amino-protecting group, instead of an HN group, and/or those which carry a hydroxyl-protecting group instead of the H atom of a hydroxyl group, for example those which conform to the formula I, but carry a —COOR" group, in which R" is a hydroxyl-protecting group, instead of a —COOH group.

Preferred starting materials are also the oxadiazole derivatives, which can be converted into the corresponding amidino compounds.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but can easily be removed after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1–20, in particular 1–8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but can easily be removed after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups is not crucial since they are removed again after the desired chemical reaction or reaction sequence; preference is given to groups having 1–20, in particular 1–10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, Obut and Mtr groups can, for example, preferably be cleaved off using TFA in dichloromethane or using approximately 3 to 5N HCl in dioxane at 15–30°, and the FMOC group can be cleaved off using an approximately 5 to 50% solution of dimethylamine, diethylamine or piperidine in DMF at 15–30°.

Protecting groups which can be removed hydrogenolytically (for example CBZ, benzyl or the liberation of the amidino group from its oxadiazole derivative)) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20–30° and 1–10 bar. Hydrogenolysis of the CBZ group succeeds well, for example, on 5 to 10% Pd/C in methanol or using ammonium formate (instead of hydrogen) on Pd/C in methanol/DMF at 20–30°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using NaOH or KOH in water, water/THF or water/dioxane, at temperatures between 0 and 100°.

Free amino and/or hydroxyl groups can furthermore be acylated in a conventional manner using an acid chloride or anhydride or alkylated using an unsubstituted or substituted alkyl halide or reacted with $CH_3$—C(=NH)—OEt, advantageously in an inert solvent, such as dichloromethane or THF and/or in the presence of a base, such as triethylamine or pyridine, at temperatures between −60 and +30°.

It is furthermore possible to convert a compound of the formula I into another compound of the formula I by converting one or more radical(s) $R^1$, $R^2$, $R^3$ and/or B into one or more other radicals $R^1$, $R^2$, $R^3$ and/or B, for example by i) cleaving an ether or ester,
ii) alkylating or acylating an OH function,
iii) reductively alkylating an amine by reaction with aldehydes and complex hydrides,
iv) reacting an amine group with malononitrile,
v) reducing a nitro group (for example by hydrogenation on Raney nickel or Pd/carbon in an inert solvent, such as methanol or ethanol) to an amino group,
vi) converting a cyano group into a tetrazole group,
vii) esterifying a carboxyl group by reaction with alcohols, and/or
viii) alkylating a nitro group under hydrogenolytic conditions, giving an alkylated amine.

Pharmaceutical Salts and Other Forms

The said compounds according to the invention can be used in their final, non-salt form. On the other hand, the present invention also covers the use of these compounds in the form of their pharmaceutically acceptable salts which can be derived from various organic and inorganic acids and bases by procedures known in the art. Pharmaceutically acceptable salt forms of the compounds of the formula I are prepared for the most part by conventional means. If the compound of the formula I contains a carboxyl group, a suitable salt thereof can be formed by reacting the compound with a suitable base to give the corresponding base-addition salt. Examples of such bases are alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. Also included are the aluminium salts of the compounds of the formula I. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide; other mineral acids and the corresponding salts thereof, such as sulfate, nitrate or phosphate, etc., and alkyl- and monoarylsulfonates, such as ethanesulfonate, toluenesulfonate and benzenesulfonate, and other organic acids and the corresponding salts thereof, such as acetate, tartrate, maleate, succinate, citrate, benzoate, salicylate, ascorbate, etc. Accordingly, the pharmaceutically acceptable acid-addition salts of the compounds of the formula I include, but are not limited to, the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate.

Furthermore, the base salts of the compounds according to the invention include, but are not limited to, aluminium, ammonium, calcium, copper, iron(III), iron(II), lithium, magnesium, manganese(III), manganese(II), potassium, sodium and zinc salts. Of the above-mentioned salts, preference is given to ammonium; the alkali metal salts sodium and potassium, and the alkaline earth metal salts calcium and magnesium. Salts of the compounds of the formula I derived from pharmaceutically acceptable organic non-toxic bases include, but are not limited to, salts of primary, secondary and tertiary amines, substituted amines, also naturally occurring substituted amines, cyclic amines and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)methylamine (tromethamine).

Compounds of the present invention which contain basic nitrogen-containing groups may be quaternised using agents, such as ($C_1$–$C_4$)alkyl halides, for example methyl, ethyl, isopropyl and tert-butyl chlorides, bromides and iodides; di($C_1$–$C_4$)alkyl sulfates, for example dimethyl, diethyl and diamyl sulfates; ($C_{10}$–$C_{18}$)alkyl halides, for example decyl, dodecyl, lauryl, myristyl and stearyl chlorides, bromides and iodides; and aryl($C_1$–$C_4$)alkyl halides, for example benzyl chloride and phenethyl bromide. Such salts enable the preparation of both water-soluble and oil-soluble compounds according to the invention.

The preferred pharmaceutical salts mentioned above include, but are not limited to, acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine.

The acid-addition salts of basic compounds of the formula I are prepared by bringing the free base form into contact with a sufficient amount of the desired acid, giving the salt in a conventional manner. The free base can be regenerated in a conventional manner by bringing the salt form into contact with a base and isolating the free base. The free base forms differ to a certain extent from the corresponding salt forms thereof in certain physical properties, such as solubility in polar solvents; otherwise, however, the salts are equivalent to their respective free base forms for the purposes of the present invention.

As mentioned, the pharmaceutically acceptable base-addition salts of the compounds of the formula I are formed with metals or amines, such as alkali metals and alkaline earth metals, or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, giving the salt in a conventional manner. The free acid can be regenerated in a conventional manner by bringing the salt form into contact with an acid and isolating the free acid. The free acid forms differ to a certain extent from the corresponding salt forms thereof in certain physical properties, such as solubility in polar solvents; otherwise, however, the salts are equivalent to their respective free acid forms for the purposes of the invention.

If a compound according to the invention contains more than one group which is capable of forming pharmaceutically acceptable salts of this type, the invention also covers multiple salts. Typical multiple salt forms include, but are not limited to, bitartrate, diacetate, difumarate, dimeglumine, diphosphate, disodium and trihydrochloride.

In view of the above, it can be seen that the expression "pharmaceutically acceptable salt" in the present connection is intended to mean an active ingredient which comprises a compound of the formula I in the form of one of its salts, in particular if this salt form provides the active ingredient with improved pharmacokinetic properties compared with the free form of the active ingredient or any other salt form of the active ingredient that has been used earlier. It may also be the case that only the pharmaceutically acceptable salt form of the active ingredient provides this active ingredient with a desired pharmacokinetic property which it did not previously possess, and may even have a positive effect on the pharmacodynamics of this active ingredient with respect to its therapeutic activity in the body.

The pharmacokinetic properties of the active ingredient which may be favourably affected include, for example, the manner in which this active ingredient is transported through cell membranes, which in turn can have a direct and positive effect on the absorption, distribution, biotransformation and excretion of this active ingredient. Although the method of administration of the pharmaceutical composition is important, and various anatomical, physiological and pathological aspects can crucially affect bioavailability, the solubility of the active ingredient is usually dependent on the nature of the particular salt form thereof which is being used. Furthermore, it is clear to the person skilled in the art that an aqueous solution of the active ingredient provides the fastest absorption of the active ingredient into the body of a patient being treated, while lipid solutions and suspensions, as well as solid dosage forms, result in less rapid absorption of the active ingredient.

Oral ingestion of an active ingredient of the formula I is the most preferred method of administration for reasons of safety, convenience and economy, but absorption of an oral dosage form of this type may be adversely affected by physical properties, such as polarity, vomiting caused by irritation of the gastrointestinal mucous membrane, degradation by digestive enzymes and low pH, irregular absorption or propulsion in the presence of food or other medicaments, and metabolism by enzymes of the mucous membrane, the intestinal flora, or the liver. Formulation of the active ingredient as different pharmaceutically acceptable salt forms may be effective in overcoming or alleviating one or more of the above-mentioned problems in connection with the absorption of oral dosage forms.

A compound of the formula I prepared by the processes described herein can be separated from the reaction mixture in which it is ultimately prepared by any desired conventional method that is familiar to the chemist in the area of organic synthesis. The separated-off compounds can be purified by known methods. Various methods and techniques can be used for the separation and purification, including, for example, distillation, re-crystallisation, column chromatography, ion-exchange chromatography, gel chromatography, affinity chromatography, preparative thin-layer chromatography and solvent extraction.

Stereoisomers

A compound which conforms to the formula I may be of such a nature that its constituent atoms are capable of being arranged spatially in two or more ways, despite having identical bonds. As a consequence, this compound exists in the form of stereoisomers. Cis/trans isomerism is only one type of stereoisomerism. If the stereoisomers are image and mirror image which cannot be superimposed, they are enantiomers which have chirality or handedness since one or more asymmetric carbon atoms are present in the structure forming them. Enantiomers are optically active and therefore distinguishable since they rotate the plane of polarised light to an equal extent, but in opposite directions.

If two or more asymmetric carbon atoms are present in a compound of the formula I, two possible configurations exist at each of these carbon atoms. If two asymmetric carbon atoms are present, four possible stereoisomers exist, for example. Furthermore, these four possible stereoisomers can be divided into six possible pairs of stereoisomers that differ from each other. In order for a pair of molecules with more than one asymmetric carbon to be enantiomers, they must have different configurations at each asymmetric carbon. Those pairs that do not behave as enantiomers have a different stereochemical relationship, which is known as a diastereomeric relationship. Stereoisomers that are not enantiomers are known as diastereoisomers, or, more frequently, diastereomers.

All of these well-known aspects of the stereochemistry of the compounds of the formula I are considered to be part of the present invention. The present invention therefore covers compounds of the formula I which are stereoisomers, and, if these are enantiomers, the individual enantiomers, racemic mixtures of these enantiomers, and artificial, i.e. synthetic, mixtures comprising proportions of these enantiomers which are different from the proportions of these enantiomers observed in a racemic mixture. If a compound of the formula I has stereoisomers that are diastereomers, this compound includes the individual diastereomers as well as mixtures of any two or more of these diastereomers in any desired proportions.

The following is intended to serve for explanation: if a single asymmetric carbon atom exists in a compound of the formula I that results in the (−)(R) and (+)(S) enantiomers thereof, this compound includes all pharmaceutically acceptable salt forms, prodrugs and metabolites thereof which are therapeutically active and useful for the treatment of or preventing the diseases and conditions described further herein. If a compound of the formula I exists in the form of (−)(R) and (+)(S) enantiomers, this compound also includes the (+)(S) enantiomer alone or the (−)(R) enantiomer alone if all, substantially all or a predominant share of the therapeutic activity resides in only one of these enantiomers or undesired side effects reside in only one of these enantiomers. If essentially no difference exists between the biological properties of the two enantiomers, this compound of the formula I furthermore includes the (+)(S) enantiomer and the (−)(R) enantiomer together as a racemic mixture or non-racemic mixture in any desired ratio of corresponding proportions.

The specific biological effects and/or physical and chemical properties of a pair or set of enantiomers of a compound of the formula I—if present—may make it obvious to use these enantiomers in certain ratios, for example to form a final therapeutic product. The following is intended to serve for illustration: if a pair of enantiomers exists, the enantiomers can be used in ratios such as 90% (R)-10% (S), 80% (R)-20% (S), 70% (R)-30% (S), 60% (R)-40% (S), 50% (R)-50% (S), 40% (R)-60% (S), 30% (R)-70% (S), 20% (R)-80% (S), and 10% (R)-90% (S). After evaluation of the properties of the various enantiomers of a compound of the formula I—if they exist—the corresponding amount of one or more of these enantiomers having certain desired properties which form the final therapeutic product can be determined in a simple manner.

Isotopes

It is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug thereof or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to their simple preparation and excellent detectability. Incorporation of heavier isotopes, for example deuterium ($^2H$), into a compound of the formula I has therapeutic advantages owing to the higher metabolic stability of this isotope-labelled compound. Higher metabolic stability translates directly into an increased in-vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant with a readily available isotope-labelled reactant.

Deuterium ($^2H$) can also be incorporated into a compound of the formula I in order to manipulate the oxidative metabolism of the compound by way of the primary kinetic isotope effect. The primary kinetic isotope effect is a change in the rate of a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom in a non-exchangeable position, rate differences of $k_M/k_D=2-7$ are typical. If this rate difference is successfully applied to a compound of the formula I that is susceptible to oxidation, the profile of this compound in vivo can thereby be drastically modified and result in improved pharmacokinetic properties.

When discovering and developing therapeutic agents, the person skilled in the art attempts to optimise pharmacokinetic parameters while retaining desirable in-vitro properties. It is reasonable to assume that many compounds with poor pharmacokinetic profiles are susceptible to oxidative metabolism. In-vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of the compounds of the formula I are thereby obtained and can be expressed quantitatively in terms of increases in the in-vivo half-life (T/2), concentration at maximum therapeutic effect ($C_{max}$), area under the dose response curve (AUC), and F; and in terms of reduced clearance, dose and costs of materials.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the undesired metabolite, even if the particular oxidation is not a rate-determining step. Further information on the state of the art with respect to deuterium-hydrogen exchange is given, for example in Hanzlik et al., J. Org. Chem. 55, 3992–3997, 1990, Reider et al., J. Org. Chem. 52, 3326–3334, 1987, Foster, Adv. Drug Res. 14,1–40, 1985, Gillette et al., Biochemistry 33 (10), 2927–2937, 1994, and Jarman et al., Carcinogenesis 16 (4), 683–688, 1993.

Therapeutic Applications

The invention furthermore relates to the use of compounds of the formula I for the treatment of myocardial diseases.

Coronary heart diseases represent the most frequent cause of death in the Western world. If the coronary vessel is critically narrowed, a decrease of blood flow may result in myocardial ischaemia. Initiation of reperfusion results, depending on the severity of the preceding ischaemic period, in a reversibly or irreversibly damaged myocardium, which is characterised by long-lasting depression or an irreversible loss of contractile function. Depending on the size of the affected myocardial area, acute or chronic heart failure may develop.

A particular clinical problem in the above-described case is the development of restenosis after initially successful reperfusion by PTCA, even after stent implantation, after thrombolysis or after transplantation of an aorto-coronary bypass. From experimental animal studies and clinical studies, there is evidence that inflammatory processes play a casual role in the various heart diseases mentioned above, i.e. coronary heart disease itself, reversible or irreversible myocardial ischaemia/reperfusion damage, acute or chronic heart failure and restenosis, including in-stent restenosis and stent-in-stent restenosis. These inflammatory processes involve resident and invading macrophages as well as neutrophils and $TH_1$ and $TH_2$ helper cells. This leukocyte response produces the characteristic cytokine pattern involving TNF-α, IL-1β, IL-2 and IL-6, as well as IL-10 and IL-13 (Pulkki K J: Cytokines and cardiomyocyte death. Ann. Med. 1997 29: 339–343.

Birks E J, Yacoub M H: The role of nitric oxide and cytokines in heart failure. Coron. Artery. Dis. 1997 8: 389–402).

The formation of this species has been demonstrated in human patients with myocardial ischaemia. Animal models show that cytokine production correlates with the invasion of peripheral macrophages and neutrophils, enabling the damage to spread into the still intact myocardium.

The main factor in the cytokine response, however, is TNF-α, which combines inflammatory and pro-apoptotic responses and additionally has a direct negative ionotropic effect on cardiac myocytes (Ceconi C, Curello S, Bachetti T, Corti A, Ferrari R: Tumor necrosis factor in congestive heart failure: a mechanism of disease for the new millennium? Prog. Cardiovasc. Dis. 1998 41: 25–30.

Mann D L: The effect of tumor necrosis factor-alpha on cardiac structure and function: a tale of two cytokines. J. Card. Fail. 1996 2: S165–S172. Squadrito F, Altavilla D, Zingarelli B, et al: Tumor necrosis factor involvement in myocardial ischaemia-reperfusion damage. Eur. J. Pharmacol. 1993 237: 223–230).

It has been shown in animal models of myocardial infarction that TNF-α is released rapidly during the reperfusion phase (Herskowitz A, Choi S, Ansari A A, Wesselingh S: Cytokine mRNA expression in postischemic/reperfused myocardium. Am. J. Pathol. 1995 146: 419–428) and that the protective effects of medicaments, such as dexamethasone (Arras M, Strasser R, Mohri M, et al.: Tumor necrosis factor-alpha is expressed by monocytes/macrophages following cardiac microembolisation and is antagonised by cyclosporine. Basic. Res. Cardiol. 1998 93: 97–107), cyclosporin A (Arras M, Strasser R, Mohri M, et al.: Tumor necrosis factor-alpha is expressed by monocytes/macrophages following cardiac microembolisation and is antagonised by cyclosporine. Basic. Res. Cardiol. 1998 93: 97–107. Squadrito F, Altavilla D, Squadrito G, et al.: Cyclosporin-A reduces leukocyte accumulation and protects against myocardial ischaemia reperfusion injury in rats. Eur. J. Pharmacol. 1999 364: 159–168) or clorichromene (Squadrito F, Altavilla D, Zingarelli B, et al.: The effect of clorichromene, a coumarine derivate, on leukocyte accumulation, myocardial necrosis and TNF-alpha production in myocardial ischaemia-reperfusion injury. Life Sci. 1993 53: 341–355), are accompanied by a reduction of circulating TNF-α.

PDE IV inhibitors of the formula I are effective antagonists of macrophage and T-cell cytokine production. They also inhibit the proliferation of T cells. PDE IV inhibition may therefore have a beneficial effect in myocardial diseases which are causally linked to cytokine production and inflammatory processes.

Compared with PDE III inhibitors and the early PDE IV inhibitor rolipram, preferred PDE IV inhibitors have no haemodynamic side effects, which can result in a restriction of the dose in the treatment of most cardiovascular disorders.

The invention had the object of finding novel potential uses of compounds having valuable properties, especially those which can be used for the preparation of medicaments.

It has been found that the compounds of the formula I and salts thereof both have extremely valuable pharmacological properties and are well tolerated for the treatment of myocardial diseases.

The invention preferably proposes the use of the compounds of the formula I for the preparation of a medicament for the treatment of myocardial diseases, where these myocardial diseases have inflammatory and immunological features.

The invention most preferably proposes the use of the compounds of the formula I for the preparation of a medicament for the treatment of coronary heart diseases, reversible or irreversible myocardial ischaemia/reperfusion damage, acute or chronic heart failure and restenosis, including in-stent restenosis and stent-in-stent restenosis.

The invention preferably proposes the use of the compounds of the formula I for the preparation of a medicament for the treatment or prevention of one or more of the diseases, pathological disorders and conditions from the following group:

asthma of whatever type, etiology or pathogenesis, or asthma selected from the group consisting of atopic asthma, non-atopic asthma, allergic asthma, atopic, IgE-mediated asthma, bronchial asthma, essential asthma, true asthma, intrinsic asthma caused by pathophysiological disturbances, extrinsic asthma caused by environmental factors, essential asthma of unknown or inapparent cause, non-atopic asthma, bronchitic asthma, emphysematous asthma, exercise-induced asthma, occupational asthma, infective asthma caused by bacterial, fungal, protozoal or viral infection, non-allergic asthma, incipient asthma, wheezy infant syndrome;

chronic or acute bronchoconstriction, chronic bronchitis, small airway obstruction and emphysema;

obstructive or inflammatory airway disease of whatever type, etiology or pathogenesis, or an obstructive or inflammatory airway disease selected from the group consisting of asthma; pneumoconiosis, chronic eosinophilic pneumonia; chronic obstructive pulmonary disease (COPD), COPD including chronic bronchitis, pulmonary emphysema or dyspnoea associated therewith, COPD that is characterised by irreversible, progressive airway obstruction, acute respiratory distress syndrome (ARDS), and exacerbation of airway hypersensitivity consequent to other medicament therapy;

pneumoconiosis of whatever type, etiology or pathogenesis, or pneumoconiosis selected from the group consisting of aluminosis, anthracosis (asthma), asbestosis, chalicosis, ptilosis caused by inhaling the dust from ostrich feathers, siderosis caused by the inhalation of iron particles, silicosis, byssinosis or cotton-dust pneumoconiosis and talc pneumoconiosis;

bronchitis of whatever type, etiology or pathogenesis, or bronchitis selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcal or streptococcal bronchitis; and vesicular bronchitis;

bronchiectasis of whatever type, etiology or pathogenesis, or bronchiectasis selected from the group consisting of cylindric bronchiectasis, sacculated bronchiectasis, fusiform bronchiectasis, capillary bronchiectasis, cystic bronchiectasis, dry bronchiectasis and follicular bronchiectasis;

seasonal allergic rhinitis, perennial allergic rhinitis, or sinusitis of whatever type, etiology or pathogenesis, or sinusitis selected from the group consisting of purulent or nonpurulent sinusitis, acute or chronic sinusitis, and ethmoid, frontal, maxillary, or sphenoid sinusitis;

rheumatoid arthritis of whatever type, etiology or pathogenesis, or rheumatoid arthritis selected from the group consisting of acute arthritis, acute gouty arthritis, primary chronic arthritis, osteoarthrosis, infectious arthritis, Lyme arthritis, progressive arthritis, psoriatic arthritis and spondylarthritis;

gout, and fever and pain associated with inflammation;

an eosinophil-related pathological disorder of whatever type, etiology or pathogenesis, or an eosinophil-related pathological disorder selected from the group consisting of eosinophilia, pulmonary infiltration eosinophilia, Löffler's syndrome, chronic eosinophilic pneumonia, tropical pulmonary eosinophilia, bronchopneumonic aspergillosis, aspergilloma, eosinophilic granuloma, allergic granulomatous angijtis or Churg-Strauss syndrome, polyarteritis nodosa (PAN) and systemic necrotising vasculitis;

atopic dermatitis, allergic dermatitis, or allergic or atopic eczema;

urticaria of whatever type, etiology or pathogenesis, or urticaria selected from the group consisting of immune-mediated urticaria, complement-mediated urticaria, urticariogenic material-induced urticaria, physical stimulus-induced urticaria, stress-induced urticaria, idiopathic urticaria, acute urticaria, chronic urticaria, angiooedema, cholinergic urticaria, cold urticaria in the autosomal dominant form or in the acquired form, contact urticaria, giant urticaria and papular urticaria;

conjunctivitis of whatever type, etiology or pathogenesis, or conjunctivitis selected from the group consisting of actinic conjunctivitis, acute catarrhal conjunctivitis, acute contagious conjunctivitis, allergic conjunctivitis, atopic conjunctivitis, chronic catarrhal conjunctivitis, purulent conjunctivitis and vernal conjunctivitis;

uveitis of whatever type, etiology or pathogenesis, or uveitis selected from the group consisting of inflammation of all or part of the uvea, anterior uveitis, iritis, cyclitis, iridocyclitis, granulomatous uveitis, nongranulomatous uveitis, phacoantigenic uveitis, posterior uveitis, choroiditis and chorioretinitis;

psoriasis;

multiple sclerosis of whatever type, etiology or pathogenesis, or multiple sclerosis selected from the group consisting of primary progressive multiple sclerosis and relapsing remitting multiple sclerosis;

autoimmune/inflammatory diseases of whatever type, etiology or pathogenesis, or an autoimmune/inflammatory disease selected from the group consisting of autoimmune haematological disorders, haemolytic anaemia, aplastic anaemia, pure red cell anaemia, idiopathic thrombocytopenic purpura, systemic lupus erythematosus, polychondritis, scleroderma, Wegner's granulomatosis, dermatomyositis, chronic active hepatitis, myasthenia gravis, Stevens-Johnson syndrome, idiopathic sprue, autoimmune inflammatory bowel diseases, ulcerative colitis, Crohn's disease, endocrine ophthamopathy, Basedow's disease, sarcoidosis, alveolitis, chronic hypersensitivity pneumonitis, primary biliary cirrhosis, juvenile diabetes or type 1 diabetes mellitus, anterior uveitis, granulomatous or posterior uveitis, keratoconjunctivitis sicca, epidemic keratoconjunctivitis, diffuse interstitial pulmonary fibrosis or interstitial pulmonary fibrosis, pulmonary cirrhosis, cystic fibrosis, psoriatic arthritis, glomerulonephritis with and without nephrotic syndrome, acute glomerulonephritis, idiopathic nephrotic syndrome, minimal change nephropathy, inflammatory/hyperproliferative skin diseases, psoriasis, atopic dermatitis, contact dermatitis, allergic contact dermatitis, benign familial pemphigus, pemphigus erythematosus, pemphigus foliaceus and pemphigus vulgaris;

prevention of foreign transplant rejection following organ transplantation;

inflammatory bowel disease (IBD) of whatever type, etiology or pathogenesis, or inflammatory bowel disease selected from the group consisting of ulcerative colitis (UC), collagenous colitis, colitis polyposa, transmural colitis and Crohn's disease (CD);

septic shock of whatever type, etiology or pathogenesis, or septic shock selected from the group consisting of renal failure, acute renal failure, cachexia, malarial cachexia, hypophysial cachexia, uremic cachexia, cardiac cachexia, cachexia suprarenalis or Addison's disease, cancerous cachexia, and cachexia as a consequence of infection by the human immunodeficiency virus (HIV);

liver damage;

pulmonary hypertension and hypoxia-induced pulmonary hypertension;

bone loss diseases, primary osteoporosis and secondary osteoporosis;

pathological disorders of the central nervous system of whatever type, etiology or pathogenesis, or a pathological disorder of the central nervous system selected from the group consisting of depression, Parkinson's disease, learning and memory disorders, tardive dyskinesia, drug dependence, arteriosclerotic dementia, and dementias that accompany Huntington's chorea, Wilson's disease, paralysis agitans and thalamic atrophies;

infections, especially viral infections, where these viruses increase the production of TNF-α in their host or where these viruses are sensitive to up-regulation of TNF-α in their host so that their replication or other vital activities are adversely affected, including viruses selected from the group consisting of HIV-1, HIV-2 and HIV-3, cytomegalovirus, CMV, influenza, adenoviruses and Herpes viruses, including Herpes zoster and Herpes simplex;

yeast and fungal infections, where these yeasts and fungi are sensitive to up-regulation by TNF-α or elicit TNF-α production in their host, for example fungal meningitis, particularly when administered in conjunction with other medicaments of choice for the treatment of systemic yeast and fungal infections, including, but not limited to, polymycins, for example polymycin B, imidazoles, for example clotrimazole, econazole, miconazole and ketoconazole, triazoles, for example fluconazole and itranazole, and amphotericins, for example amphotericin B and liposomal amphotericin B;

ischaemia-reperfusion damage, autoimmune diabetes, retinal autoimmunity, chronic lymphocytic leukaemia, HIV infections, lupus erythematosus, kidney and ureter diseases, pathological urogenital and gastrointestinal disorders and prostate diseases.

In particular, compounds of the formula I are suitable for the treatment of (1) inflammatory diseases and conditions, including joint inflammation, rheumatoid arthritis, rheumatoid spondylitis, osteoarthritis, inflammatory bowel disease, ulcerative colitis, chronic glomerulonephritis, dermatitis and Crohn's disease, (2) respiratory tract diseases and conditions, including asthma, acute respiratory distress syndrome, chronic pulmonary inflammatory disease, bronchitis, chronic obstructive airway disease and silicosis, (3) infectious diseases and conditions, including sepsis, septic shock, endotoxic shock, Gram-negative sepsis, toxic shock syndrome, fever and myalgias due to bacterial, viral or fungal infection, and influenza, (4) immune diseases and conditions, including autoimmune diabetes, systemic lupus erythematosis, GvH reaction, rejection of foreign transplants, multiple sclerosis, psoriasis and allergic rhinitis, and (5) other diseases and conditions, including bone absorption diseases, reperfusion damage, cachexia secondary to infection or malignancy, cachexia secondary to human acquired immune deficiency syndrome (AIDS), human immunodeficiency virus (HIV) infection, or AIDS related complex (ARC), keloid formation, scar tissue formation, type 1 diabetes mellitus and leukaemia.

The present invention furthermore relates to the combination of a compound of the formula I together with one or more members selected from the group consisting of the following:

(a) leukotriene biosynthesis inhibitors: 5-lipoxygenase (5-LO) inhibitors and 5-lipoxygenase activating protein (FLAP) antagonists selected from the group consisting of zileuton, ABT-761, fenleuton, tepoxalin, Abbott-79175, Abbott-85761, N-(5-substituted)-thiophene-2-alkylsulfonamides, 2,6-di-tert-butylphenol hydrazones, the class of the methoxytetrahydropyrans, including Zeneca ZD-2138, the compound SB-210661 and the class to which it belongs, the class of the pyridinyl-substituted 2-cyanonaphthalene compounds, including L 739,010, the class of the 2-cyanoquinoline compounds, including L-746,530, the classes of the indole and quinoline compounds, including MK-591, MK-886 and BAY×1005;

(b) receptor antagonists for the leukotrienes $LTB_4$, $LTC_4$, $LTD_4$ and $LTE_4$ selected from the group consisting of the class of the phenothiazin-3-one compounds, including L-651,392, the class of the amidino compounds, including CGS-25019c, the class of the benzoxazolamines, including ontazolast, the class of the benzenecarboximideamides, including BIIL 284/260, and the classes of compound to which zafirlukast, ablukast, montelukast, pranlukast, verlukast (MK-679), RG-12525, Ro-245913, iralukast (CGP 45715A) and BAY×7195 belong; (c) PDE IV inhibitors;

(d) 5-lipoxygenase inhibitors (5-LO); or 5-lipoxygenase activating protein (FLAP) antagonists; (e) dual inhibitors of 5-lipoxygenase (5-LO) and antagonists of platelet activating factor (PAF); (f) leukotriene antagonists (LTRAs) including $LTB_4$, $LTC_4$, $LTD_4$ and $LTE_4$ antagonists; (g) antihistamine $H_1$ receptor antagonists, including cetirizine, loratadine, desloratadine, fexofenadine, astemizole, azelastine and chlorpheniramine; (h) gastroprotective $H_2$ receptor antagonists; (i) $α_1$- and $α_2$-adrenoreceptor agonist vasoconstrictor sympathomimetic agents administered orally or topically for decongestant use, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride and ethylnorepinephrine hydrochloride; j) $α_1$- and $α_2$-adrenoreceptor agonists in combination with inhibitors of 5-lipoxygenase (5-LO); (k) anticholinergic agents, including ipratropium bromide, tiotropium bromide, oxitropium bromide, pirenzepine and telenzepine; (l) $β_1$- to $β_4$ adrenoreceptor agonists, including metaproterenol, isoproterenol, isoprenaline, albuterol, salbutamol, formoterol, salmeterol, terbutaline, orciprenaline, bitolterol mesylate and pirbuterol; (m) methylxanthanines, including theophylline and aminophylline; (n) sodium cromoglycate; (O) muscarinic receptor (M1, M2 and M3) antagonists; (p) COX-1 inhibitors (NSAIDs); COX-2 selective inhibitors, including rofecoxib, and nitric oxide NSAIDs; (q) insulin-like growth factor type I (IGF-1) mimetics; (r) ciclesonide; (s) inhalation glucocorticoids with reduced systemic side effects, including prednisone, prednisolone, flunisolide, triamcinolone acetonide, beclomethasone dipropionate, budesonide, fluticasone propionate and mometasone furoate; (t) tryptase inhibitors; (u) platelet activating factor (PAF) antagonists; (v) monoclonal antibodies against endogenous inflammatory entities; (w) IPL 576; (x) antitumour necrosis factor (TNFα) agents, including etanercept, infliximab and D2E7; (y) DMARDs, including leflunomide; (z) TCR peptides; (aa) interleukin converting enzyme (ICE) inhibitors; (bb) IMPDH inhibitors; (cc) adhesion molecule inhibitors, including VLA-4 antagonists; (dd) cathepsins; (ee) MAP kinase inhibitors; (ff) glucose 6-phosphate dehydrogenase inhibitors; (gg) kinin $B_1$ and $B_2$ receptor antagonists; (hh) gold in the form of an aurothio group together with various hydrophilic groups; (ii) immunosuppressive agents, for example cyclosporine, azathioprine and methotrexate; (jj) anti-gout agents, for example colchicine; (kk) xanthine oxidase inhibitors, for example allopurinol; (ll) uricosuric agents, for example probenecide, sulfinpyrazone and benzbromarone; (mm) antineoplastic agents, especially antimitotic medicaments, including the vinca alkaloids, such as vinblastine and vincristine; (nn) agents for promoting the secretion of growth hormone; (oo) inhibitors of matrix metalloproteases (MMPs), i.e. the stromelysins, collagenases and gelatinases, as well as aggrecariase, especially collagenase-1 (MMP-1), collagenase-2 (MMP-8), collagenase-3 (MMP-13), stromelysin-1 (MMP-3), stromelysin-2 (MMP-10) and stromelysin-3 (MMP-11); (pp) transforming growth factor (TGFβ); (qq) platelet-derived growth factor (PDGF); (rr) fibroblast growth factor, for example basic fibroblast growth factor (bFGF); (ss) granulocyte macrophage colony stimulating factor (GM-CSF); (tt) capsaicin; (uu) tachykinin NK$_1$ and NK$_3$ receptor antagonists selected from the group consisting of NKP-608C; SB233412 (talnetant) and D-4418; and (w) elastase inhibitors selected from the group consisting of UT-77 and ZD-0892.

The present invention relates to a combination of a compound of the formula I together with one or more additional therapeutic agents for joint administration to a patient in order to obtain a particularly desired therapeutic end result. The second, etc. therapeutic agent may likewise be one or more compounds as described above or one or more PDE IV inhibitors known in this art and described in greater detail here. In particular, the second, etc. therapeutic agent is selected from a different class of therapeutic agents. These selected combinations are described in greater detail below.

In the present connection, the terms "joint administration", "jointly administered" and "in combination with", if they refer to the compounds of the formula I and one or more other therapeutic agents, should be taken to mean the following and do refer to and include the following:

(a) simultaneous administration of such a combination of one or more compound(s) and a therapeutic agent or a plurality of therapeutic agents to a patient in need of treatment if these components are formulated jointly as a single dosage form which releases these components to the patient at essentially the same time, (b) essentially simultaneous administration of such a combination of one or more compound(s) and a therapeutic agent or a plurality of therapeutic agents to a patient in need of treatment if these components are formulated separately as separate dosage forms which are taken by the patient at essentially the same time, and the components are released to this patient at essentially the same time;

(c) sequential administration of such a combination of one or more compound(s) and a therapeutic agent or a plurality of therapeutic agents to a patient in need of treatment if these components are formulated separately from one another as separate dosage forms which are taken by the patient at successive times with a clear time interval between each taking, and the components are released to the patient at essentially different times; and (d) sequential administration of such a combination of one or more compound(s) and a therapeutic agent or a plurality of therapeutic agents to a patient in need of treatment if these components are formulated jointly as a single dosage form which releases these components in a controlled manner, and the components are taken by the patient simultaneously, successively and/or in an overlapping manner at the same time and/or at different times.

Combinations with Leukotriene Biosynthesis Inhibitors: 5-lipoxygenase (5-LO) Inhibitors and 5-lipoxygenase Activating Protein (FLAP) Antagonists In order to form embodiments according to the invention, one or more of the compounds of the formula I is (are) used in combination with leukotriene biosynthesis inhibitors, i.e. 5-lipoxygenase inhibitors or 5-lipoxygenase activating protein antagonists. 5-Lipoxygenase (5-LO) is one of two groups of enzymes which metabolise arachidonic acid, the other group being the cyclooxygenases, COX-1 and COX-2.

5-lipoxygenase activating protein is a membrane-bound, arachidonate-binding protein with a size of 18 kDa which stimulates the conversion of arachidonic acid in the cell by 5-lipoxygenase. The arachidonic acid is converted into 5-hydroperoxyeicosatetraenoic acid (5-HPETE), and this route ultimately leads to the production of inflammatory leukotrienes; blocking of 5-lipoxygenase activating protein or the enzyme 5-lipoxygenase itself therefore represents a desirable aim for favourably influencing this route. One of these 5-lipoxygenase inhibitors is zileuton.

The classes of leukotriene synthesis inhibitors which are suitable for the formation of therapeutic combinations with the compounds of the formula I include the following:

(a) redox-active agents, including N-hydroxyureas, N-alkylhydroxamide acids, selenite, hydroxybenzofurans, hydroxylamines and catechol, see Ford-Hutchinson et al., "5-Lipoxygenase", Ann. Rev. Biochem. 63, 383–417, 1994; Weitzel and Wendel, "Selenoenzymes regulate the activity of leukocyte 5-lipoxygenase via the peroxide tone", J. Biol. Chem. 268, 6288–92, 1993; Björnstedt et al. "Selenite incubated with NADPH and mammalian thioredoxin reductase yields selenide, which inhibits lipoxygenase and changes the electron spin resonance spectrum of the active site iron", Biochemistry 35, 8511–6, 1996, and Stewart et al., "Structure-activity relationships of N-hydroxyurea 5-lipoxygenase inhibitors", J. Med. Chem. 40, 1955–68, 1997;

(b) alkylating agents and compounds which react with SH groups have been found to inhibit leukotriene synthesis in vitro; see. Larsson et al., "Effects of 1-chloro-2,4,6-trinitrobenzene on 5-lipoxygenase activity and cellular leukotriene synthesis", Biochem. Pharmacol. 55, 863–71, 1998; and (c) competitive inhibitors of 5-lipoxygenase based on thiopyranoindole and methoxyalkyl thiazole structures which act as non-redox inhibitors of 5-lipoxygenase; see Ford-Hutchinson et al., ibid.; and Hamel et al., "Substituted (pyridylmethoxy)naphthalenes as potent and orally active 5-lipoxygenase inhibitors—synthesis, biological profile and pharmacokinetics of L-739,010", J. Med. Chem. 40, 2866–75, 1997.

The observation that arachidonic acid hydroxamate inhibits 5-lipoxygenase has led to the discovery of clinically useful selective 5-lipoxygenase inhibitors, such as the N-hydroxyurea derivatives zileuton and ABT-761, which are shown below:

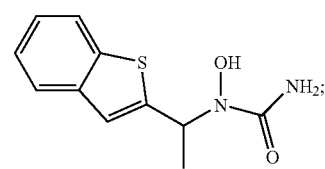

Zileuton

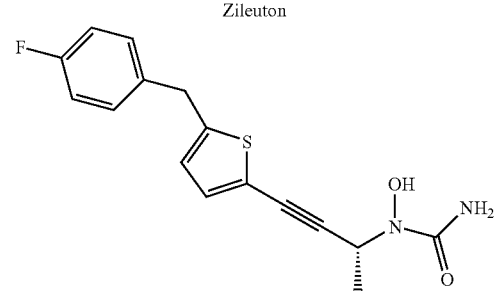

ABT-761

Another N-hydroxyurea compound is fenleuton (Abbott-76745):

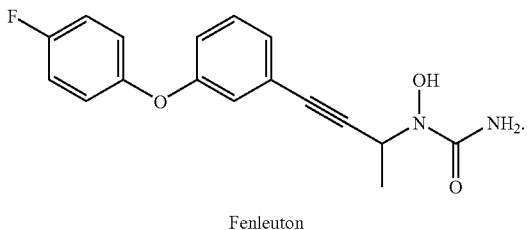

Fenleuton

Another N-hydroxyurea compound is Abbott-79175

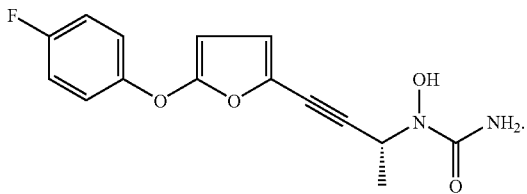

Abbott-79175

Abbott-79175 has a longer duration of action than zileuton; Brooks et al., J. Pharm. Exp. Therapeut 272–724, 1995. Yet another N-hydroxyurea compound is Abbott-85761

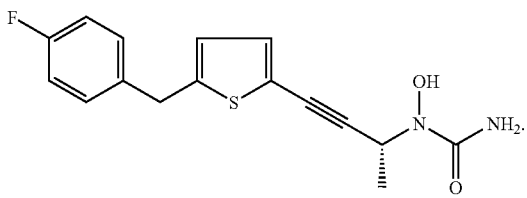

Abbott-85761

Abbott-85761 is delivered to the lung by aerosol administration of a homogeneous, physically stable and virtually monodisperse formulation; Gupta et al., "Pulmonary delivery of the 5-lipoxygenase inhibitor, Abbott-85761, in beagle dogs", International Journal of Pharmaceutics 147, 207–218, 1997.

For the formation of embodiments according to the invention, fenleuton, Abbott-79175, Abbott-85761 or any of the above-described derivatives thereof or tepoxalin derivatives are combined with the compounds of the formula I.

Since the elucidation of the 5-LO biosynthetic pathway, there has been an ongoing debate as to whether it is more advantageous to inhibit the 5-lipoxygenase enzyme or to use antagonists for the peptido- or non-peptidoleukotriene receptors. Inhibitors of 5-lipoxygenase are thought to be superior to LT receptor antagonists, since 5-lipoxygenase inhibitors block the action of the entire range of 5-LO products, whereas the action of LT antagonists is narrower. Nevertheless, embodiments according to the invention include combinations of the compounds of the formula I not only with 5-LO inhibitors, but also with LT antagonists, as described below. Inhibitors of 5-lipoxygenase having chemical structures which differ from the classes of N-hydroxyureas and hydroxamic acids described above are likewise combined with the compounds of the formula I and thus form further embodiments according to the invention. An example of a different class of this type comprises the N-(5-substituted)-thiophene-2-alkylsulfonamides of the formula

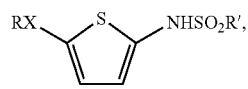

in which X is O or S; R' is methyl, isopropyl, n-butyl, n-octyl or phenyl, and R is n-pentyl, cyclohexyl, phenyl, tetrahydro-1-naphthyl, 1- or 2-naphthyl, or phenyl which is monosubstituted or disubstituted by Cl, F, Br, $CH_3$, $OCH_3$, $SCH_3$, $SO_2CH_3$, $CF_3$, or isopropyl. A preferred compound is

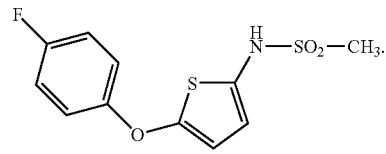

A more precise description of these compounds is given in Beers et al., "N-(5-substituted) thiophene-2-alkylsulfonamides as potent inhibitors of 5-lipoxygenase", Bioorganic & Medicinal Chemistry 5 (4), 779–786, 1997.

Another different class of 5-lipoxygenase inhibitors is the class of the 2,6-di-tert-butylphenol hydrazones which is described in Cuadro et al., "Synthesis and biological evaluation of 2,6-di-tert-butylphenol hydrazones as 5-lipoxygenase inhibitors", Bioorganic & Medicinal Chemistry 6, 173–180, 1998. Compounds of this type conform to the formula

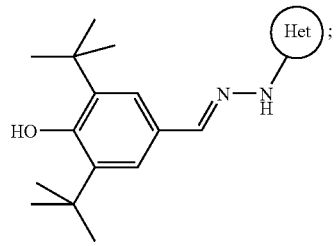

in which "Het" is benzoxazol-2-yl, benzothiazol-2-yl, pyridin-2-yl, pyrazin-2-yl, pyrimidin-2-yl, 4-phenylpyrimidin-2-yl, 4,6-diphenylpyrimidin-2-yl, 4-methylpyrimidin-2-yl, 4,6-dimethylpyrimidin-2-yl, 4-butylpyrimidin-2-yl, 4,6-dibutylpyrimidin-2-yl and 4-methyl-6-phenylpyrimidin-2-yl.

The N-(5-substituted)-thiophene-2-alkylsulfonamides or the 2,6-di-tert-butylphenol hydrazones or any of the above-described derivatives thereof are combined with the compounds of the formula I mentioned above and thus form embodiments according to the invention.

A further different class of 5-lipoxygenase inhibitors is that of the methoxytetrahydropyrans to which Zeneca ZD-2138 belongs

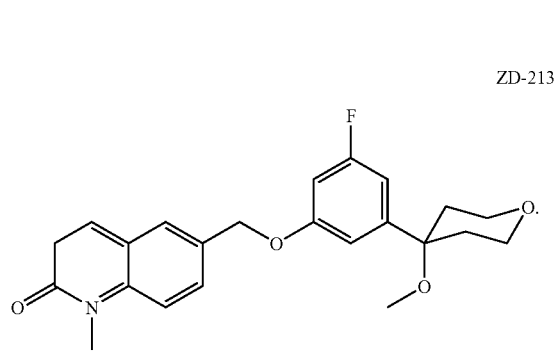

ZD-2138

ZD-2138 is highly selective and highly active on oral administration in various species and has been evaluated in the treatment of asthma and rheumatoid arthritis by oral administration. Further details concerning ZD-2138 and derivatives thereof are given in Crawley et al., J. Med. Chem., 35, 2600, 1992, and Crawley et al., J. Med. Chem. 36, 295, 1993.

Another different class of 5-lipoxygenase inhibitors is that comprising the SmithKline Beecham compound SB-210661

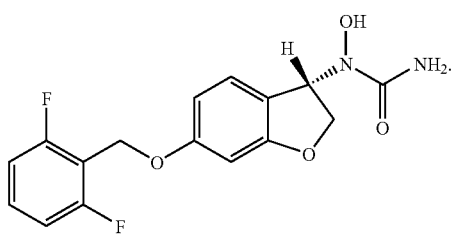

Two further different, related classes of 5-lipoxygenase inhibitors comprise various pyridinyl-substituted 2-cyanonaphthalene compounds and various 2-cyanoquinoline compounds which were discovered by Merck Frosst. These two classes of 5-lipoxygenase inhibitors are illustrated by L-739,010 and L-746,530, respectively:

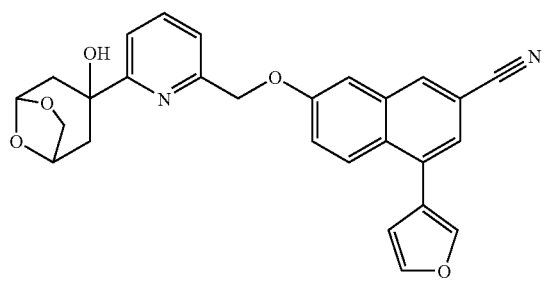

L-739,010

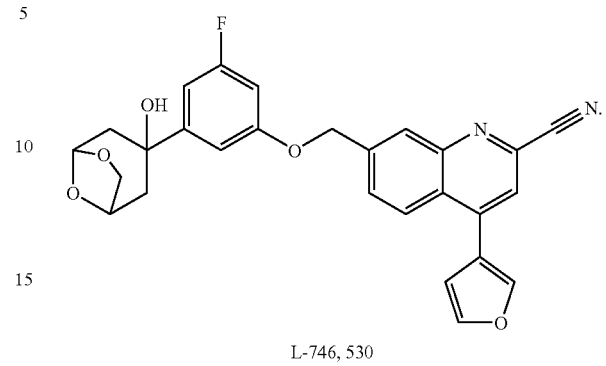

L-746,530

Further details concerning L-739,010 and L-746,530 are given in Dubé et al., "Quinolines as potent 5-lipoxygenase inhibitors: synthesis and biological profile of L-746,530", Bioorganic & Medicinal Chemistry 8, 1255–1260, 1998, and in WO 95/03309 (Friesen et al.).

The class of the methoxytetrahydropyrans, including Zeneca ZD-2138, or the lead compound SB-210661 and the class to which it belongs, or the series of pyridinyl-substituted 2-cyanonaphthalene compounds, including L-739,010, or the series of 2-cyanoquinoline compounds, including L-746,530, or any of the above-described derivatives of any of the above-mentioned classes, are combined with the compounds of the formula I and thus form embodiments according to the invention.

The other endogenous substance which, besides the 5-lipoxygenase enzyme, plays a significant role in leukotriene biosynthesis is 5-lipoxygenase activating protein (FLAP). In contrast to the direct role of the 5-lipoxygenase enzyme, this protein has an indirect role. Nevertheless, antagonists of 5-lipoxygenase activating protein are used to inhibit leukotriene synthesis in the cell and as such they are also used in combination with the compounds of the formula I and thus form embodiments according to the invention.

Compounds which bind to 5-lipoxygenase activating protein and thus block utilisation of the endogenous pool of arachidonic acid which is present have been synthesised from indole and quinoline structures; see Ford-Hutchinson et al., ibid., Rouzer et al. "WK-886, a potent and specific leukotriene biosynthesis inhibitor blocks and reverses the membrane association of 5-lipoxygenase in ionophore-challenged leukocytes", J. Biol. Chem. 265,1436–42, 1990, and Gorenne et al., "{(R)-2-quinolin-2-yl-methoxy)phenyl)-2-cyclopentyl acetic acid} (BAY×1005), a potent leukotriene synthesis inhibitor: effects on anti-IgE challenge in human airways", J. Pharmacol. Exp. Ther. 268, 868–72, 1994.

MK-591, with the name quiflipon sodium, conforms to the formula

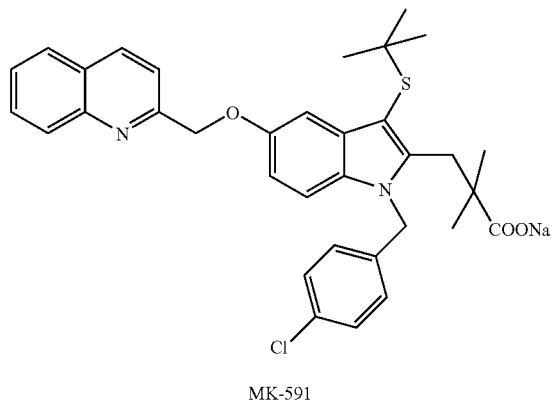

MK-591

The above-mentioned indole and quinoline classes of compounds, including the specific compounds MK-591, MK-886 and BAYx1005, or any of the above-described derivatives of any of the above-mentioned classes, are combined with the compounds of the formula I and thus form embodiments according to the invention.

Combinations with Receptor Antagonists for the Leukotrienes $LTB_4$, $LC_4$, $LTD_4$ and $LTE_4$ A compound of the formula I or a plurality of compounds of the formula I is or are used in combination with receptor antagonists for the leukotrienes $LTB_4$, $LTC_4$, $LTD_4$ and $LTE_4$. The most significant of these leukotrienes in terms of mediating an inflammatory response are $LTB_4$ and $LTD_4$. Classes of antagonists for the receptors of these leukotrienes are described in the paragraphs which follow.

4-Bromo-2,7-dimethoxy-3H-phenothiazin-3-ones, including L-651,392, are effective $LTB_4$ antagonists which are described in U.S. Pat. No. 4,939,145 (Guindon et al.) and U.S. Pat. No. 4,845,083 (Lau et al.)

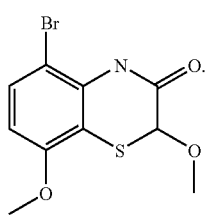

L-651, 392

A class of amidino compounds, which includes CGS-25019c, is described in U.S. Pat. No. 5,451,700 (Morrissey and Suh); U.S. Pat. No. 5,488,160 (Morrissey), and U.S. Pat. No. 5,639,768 (Morrissey and Suh). A typical representative of these $LTB_4$ antagonists is CGS-25019c, which is shown below:

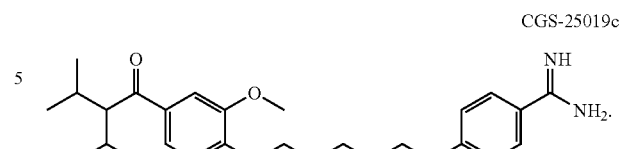

CGS-25019c

Ontazolast, a member of a class of benzoxaolamines which are $LTB_4$ antagonists, is described in EP 535 521 (Anderskewitz et al.):

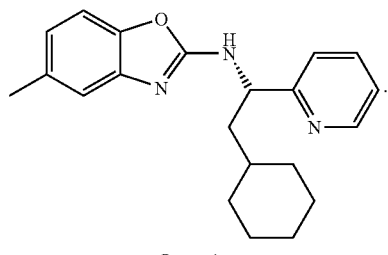

Ontozolast

The same working group also discovered a class of benzenecarboximideamides which are $LTB_4$ antagonists, which are described in WO 97/21670 (Anderskewitz et al.) and WO 98/11119 (Anderskewitz et al.) and of which BIIL 284/260 is a typical representative:

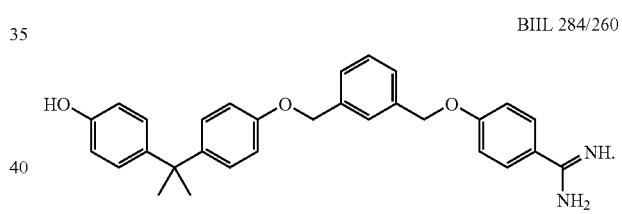

BIIL 284/260

Zafirlukast is an $LTC_4$, $LTD_4$ and $LTE_4$ receptor antagonist which is commercially available under the name Accolate®. It belongs to a class of heterocyclic amide derivatives which is described in U.S. Pat. No. 4,859,692 (Bernstein et al.), U.S. Pat. No. 5,319,097 (Holohan and Edwards), U.S. Pat. No. 5,294,636 (Edwards and Sherwood), U.S. Pat. No. 5,482,963; U.S. Pat. No. 5,583,152 (Bernstein et al.) and U.S. Pat. No. 5,612,367 (Timko et al.):

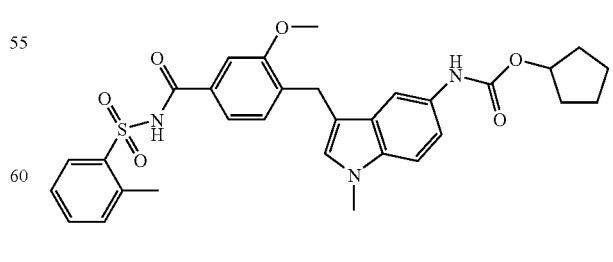

Zafirlukast

Ablukast is an $LTD_4$ receptor antagonist which carries the designation Ro 23-3544/001:

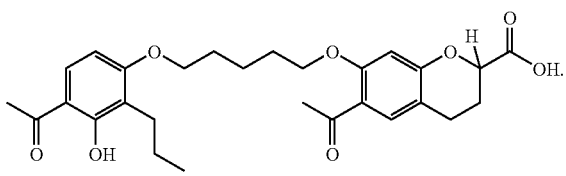

Ablukast

Montelukast is an LTD$_4$ receptor antagonist which is commercially available under the name Singulair® and is described in U.S. Pat. No. 5,565,473:

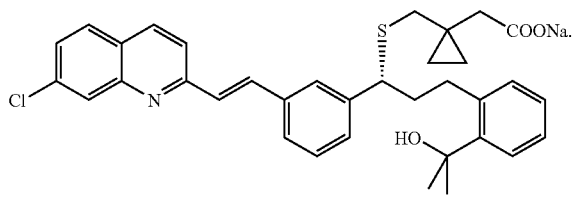

Montekulast

Other LTD$_4$ receptor antagonists include pranlukast, verlukast (MK-679), RG-12525, Ro-245913, iralukast (CGP 45715A) and BAYx7195.

The above-mentioned phenothiazin-3-one class of compounds, including L-651,392, the class of the amidino compounds, including CGS-25019c, the class of the benzoxazolamines, which includes ontazolast, the class of the benzenecarboximideamides, which is typified by BIIL 284/260, the heterocyclic amide derivatives, including zafirlukast, ablukast and montelukast, and the classes of compounds to which they belong, or any of the above-described derivatives of any of the above-mentioned classes, are combined with the compounds of the formula I and thus form embodiments according to the invention.

Combinations with Other Therapeutic Agents

One or more compounds of the formula I are used together with other therapeutic agents as well as non-therapeutic agents and combinations are thus formed which are further embodiments according to the invention and which are suitable for the treatment of a whole series of different diseases, pathological disorders and conditions described herein. These embodiments include one or more compounds of the formula I together with one or more of the following substances:

(a) PDE IV inhibitors;
(b) 5-lipoxygenase (5-LO) inhibitors or 5-lipoxygenase activating protein (FLAP) antagonists;
(c) dual inhibitors of 5-lipoxygenase (5-LO) and antagonists of platelet activating factor (PAF);
(d) leukotriene antagonists (LTRAs), including LTB$_4$, LTC$_4$, LTD$_4$ and LTE$_4$ antagonists;
(e) antihistamine H$_1$ receptor antagonists, including cetirizine, loratadine, desloratadine, fexofenadine, astemizole, azelastine and chlorpheniramine;
(f) gastroprotective H$_2$ receptor antagonists;
(g) $\alpha_1$- and $\alpha_2$-adrenoreceptor agonist vasoconstrictor sympathomimetic agents administered orally or topically for decongestant use, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride and ethylnorepinephrine hydrochloride;
(h) $\alpha_1$- and $\alpha_2$-adrenoreceptor agonists in combination with inhibitors of 5-lipoxygenase (5-LO);
(i) anticholinergic agents, including ipratropium bromide, tiotropium bromide, oxitropium bromide, pirenzepine and telenzepine;
(j) $\beta_1$- to $\beta_4$-adrenoreceptor agonists, including metaproterenol, isoproterenol, isoprenaline, albuterol, salbutamol, formoterol, salmeterol, terbutaline, orciprenaline, bitolterol mesylate and pirbuterol;
(k) theophylline and aminophylline;
(l) sodium cromoglycate;
(m) muscarinic receptor (M1, M2 and M3) antagonists;
(n) COX-1 inhibitors (NSAIDs); COX-2 selective inhibitors, including rofecoxib, and nitric oxide NSAIDs;
(o) insulin-like growth factor type I (IGF-1) mimetics;
(p) ciclesonide;
(q) inhalation glucocorticoids with reduced systemic side effects, including prednisone, prednisolone, flunisolide, triamcinolone acetonide, beclomethasone dipropionate, budesonide, fluticasone propionate and mometasone furoate;
(r) tryptase inhibitors;
(s) platelet activating factor (PAF) antagonists;
(t) monoclonal antibodies against endogenous inflammatory entities;
(u) IPL 576;
(v) antitumour necrosis factor (TNFα) agents, including etanercept, infliximab and D2E7;
(w) DMARDs, including leflunomide;
(x) TCR peptides;
(y) interleukin converting enzyme (ICE) inhibitors;
(z) IMPDH inhibitors;
(aa) adhesion molecule inhibitors, including VLA-4 antagonists;
(bb) cathepsins;
(cc) MAP kinase inhibitors;
(dd) glucose 6-phosphate dehydrogenase inhibitors;
(ee) kinin B$_1$, and B$_2$ receptor antagonists;
(ff) gold in the form of an aurothio group together with various hydrophilic groups;
(gg) immunosuppressive agents, for example cyclosporine, azathioprine and methotrexate;
(hh) anti-gout agents, for example colchicine;
(ii) xanthine oxidase inhibitors, for example allopurinol;
(jj) uricosuric agents, for example probenecide, sulfinpyrazone and benzbromarone;
(kk) antineoplastic agents, especially antimitotic medicaments, including the vinca alkaloids, such as vinblastine and vincristine;
(ll) agents for promoting growth hormone secretion;
(mm) inhibitors of matrix metalloproteases (MMPs), i.e. the stromelysins, collagenases and gelatinases, as well as aggrecanase, especially collagenase-1 (MMP-1), collagenase-2 (MMP-8), collagenase-3 (MMP-13), stromelysin-1 (MMP-3), stromelysin-2 (MMP-10) and stromelysin-3 (MMP-11);
(nn) transforming growth factor (TGFβ);
(oo) platelet-derived growth factor (PDGF);
(pp) fibroblast growth factor, for example basic fibroblast growth factor (bFGF);
(qq) granulocyte macrophage colony stimulating factor (GM-CSF);
(rr) capsaicin;

(ss) tachykinin $NK_1$ and $NK_3$ receptor antagonists selected from the group consisting of NKP-608C; SB233412 (talnetant) and D-4418;

(tt) elastase inhibitors selected from the group consisting of UT-77 and ZD-0892, and (uu) adenosine A2a receptor agonists.

Pharmaceutical Compositions and Formulations

The description which follows relates to the manner in which the compounds of the formula I, if desired together with other therapeutic agents or non-therapeutic agents, are combined with predominantly conventional pharmaceutically acceptable excipients to form dosage forms which are suitable for the different methods of administration which are utilised for any given patient, and appropriate to the disease, pathological disorder or condition for which a given patient is being treated.

The pharmaceutical compositions according to the invention comprise any one or more of the above-described inhibitor compounds according to the invention or a pharmaceutically acceptable salt thereof as also described above, together with a pharmaceutically acceptable excipient in accordance with the properties and expected behaviour of such excipients which are well known to the person skilled in the art.

The amount of active ingredient that can be combined with the excipient materials to form a single dosage form varies depending upon the patient being treated and the particular method of administration. However, it is clear that a certain dosage and treatment regime for a particular patient depends on a wide variety of factors, including the efficacy of the particular compound used, the age, body weight, general state of health, sex, the diet, the time of administration, the excretion rate, medicament combination, and the judgment of the treating physician and the severity of the particular disease being treated. The amount of active ingredient may also depend on the therapeutic or prophylactic agent, if any, with which the active ingredient is jointly administered.

The compounds of the formula I can be used in the form of acids, esters, or other chemical classes of compounds to which the compounds described belong. It is also within the scope of the present invention to use these compounds in the form of pharmaceutically acceptable salts derived from various organic and inorganic acids and bases. An active ingredient comprising a preferred compound is often used in the form of one of its salts, in particular if this salt form provides the active ingredient with improved pharmacokinetic properties compared with the free form of the active ingredient or another salt form of the active ingredient used previously. It may also be the case that only the pharmaceutically acceptable salt form of the active ingredient provides this active ingredient with a desired pharmacokinetic property which it did not previously possess, and may even have a positive effect on the pharmacodynamics of this active ingredient with respect to its therapeutic activity in the body.

The pharmacokinetic properties of the active ingredient which may be favourably affected include, for example, the manner in which this active ingredient is transported through cell membranes, which in turn can have a direct and positive effect on the absorption, distribution, biotransformation and excretion of this active ingredient. Although the method of administration of the pharmaceutical composition is important, and various anatomical, physiological and pathological aspects can crucially affect bioavailability, the solubility of the active ingredient is usually dependent on the nature of the particular salt form thereof which is being used. Furthermore, it is clear to the person skilled in the art that an aqueous solution of the active ingredient provides the fastest absorption of the active ingredient into the body of a patient being treated, while lipid solutions and suspensions, as well as solid dosage forms, result in less rapid absorption of the active ingredient. Oral ingestion of an active ingredient of the formula I is the most preferred method of administration for reasons of safety, convenience and economy, but absorption of an oral dosage form of this type may be adversely affected by physical properties, such as polarity, vomiting caused by irritation of the gastrointestinal mucous membrane, degradation by digestive enzymes and low pH, irregular absorption or propulsion in the presence of food or other medicaments, and metabolism by enzymes of the mucous membrane, the intestinal flora, or the liver. Formulation of the active ingredient as different pharmaceutically acceptable salt forms may be effective in overcoming or alleviating one or more of the above-mentioned problems in connection with the absorption of oral dosage forms.

The preferred pharmaceutical salts mentioned above include, but are not limited to, acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine.

If a compound of the formula I contains more than one group which is capable of forming pharmaceutically acceptable salts of this type, the invention also covers multiple salts. Typical multiple salt forms include, but are not limited to, bitartrate, diacetate, difumarate, dimeglumine, diphosphate, disodium and trihydrochloride.

The pharmaceutical compositions according to the invention comprise one or more of the above-described inhibitor compounds or a pharmaceutically acceptable salt thereof as also described above, together with a pharmaceutically acceptable excipient in accordance with the properties and expected behaviour of such excipients which are well known to the person skilled in the art.

The term "excipient" in the present connection includes acceptable diluents, carriers, adjuvants, constituents, solubilisers, viscosity modifiers, preservatives and other agents which are well known to the person skilled in the art for providing the final pharmaceutical composition with favourable properties. In order to illustrate these excipients, there follows a brief review of pharmaceutically acceptable excipients which can be used in the pharmaceutical compositions according to the invention, and thereafter a more detailed description of the various types of constituents. Typical excipients include, but are by no means limited to, the following: ion exchange compositions, alumina, aluminium stearate, lecithin, serum proteins, for example human serum albumin, phosphates, glycine, sorbic acid, potassium sorbate, partial glyceride mixtures of saturated vegetable fatty acids, hydrogenated palm oils, water, salts or electrolytes, for example prolamine sulfate, disodium hydrogenphosphate, potassium hydrogenphosphate, sodium chloride and zinc salts, colloidal silica, magnesium trisilicate, polyvinylpyrrolidone, cellulose-based substances, for example sodium carboxymethylcellulose, polyethylene glycol, polyacrylates, waxes, polyethylene-polyoxypropylene block polymers and wool fat.

In particular, the excipients used in the pharmaceutical compositions according to the invention includes various classes and types of additives which are selected independently from the groups essentially mentioned in the following paragraphs.

Acidifying and alkalising agents are added to obtain a desired or predetermined pH; they comprise acidifying agents, for example acetic acid, glacial acetic acid, malic acid and propionic acid. Stronger acids, such as hydrochloric acid, nitric acid and sulfuric acid, can be used, but are less preferred. Alkalising agents include, for example, edetol, potassium carbonate, potassium hydroxide, sodium borate, sodium carbonate and sodium hydroxide. Alkalising agents which contain active amino groups, such as diethanolamine and trolamine, can also be used.

Aerosol propellants are required if the pharmaceutical composition is to be delivered as an aerosol under considerable pressure. Such propellants include, for example, acceptable chlorofluorocarbons, such as dichlorodifluoromethane, dichlorotetrafluoroethane and trichloromonofluoromethane, nitrogen, a volatile hydrocarbon, such as butane, propane or isobutane, or mixtures thereof.

Antimicrobial agents, including antibacterial, antifungal and antiprotozoal agents, are added if the pharmaceutical composition is applied topically to areas of the skin which are likely to have been exposed to a harmful environment or sustained abrasions or cuts which makes the skin susceptible to infection by bacteria, fungi or protozoa. Antimicrobial agents include compounds, such as benzyl alcohol, chlorobutanol, phenylethyl alcohol, phenylmercuric acetate, potassium sorbate and sorbic acid. Antifungal agents include compounds, such as benzoic acid, butylparaben, ethylparaben, methylparaben, propylparaben and sodium benzoate.

Antimicrobial preservatives are added to the pharmaceutical compositions according to the invention in order to protect them against the growth of potentially harmful microorganisms, which usually invade the aqueous phase, but in some cases can also grow in the oil phase of a composition. Thus, preservatives with both aqueous and lipid solubility are desired. Suitable antimicrobial preservatives include, for example, alkyl p-hydroxybenzoates, propionate salts, phenoxyethanol, methylparabensodium, propylparaben-sodium, sodium dehydroacetate, benzalkonium chloride, benzethonium chloride, benzyl alcohol, hydantoin derivatives, quaternary ammonium compounds and cationic polymers, imidazolidinylurea, diazolidinylurea and trisodium ethylenediamine tetraacetate (EDTA). Preservatives are preferably employed in amounts of from about 0.01% by weight to about 2.0% by weight of the total composition.

Antioxidants are added to protect all the constituents of the pharmaceutical composition from damage or degradation by oxidants present in the composition itself or in the environment in which they are used, for example anoxomer, ascorbyl palmitate, butylhydroxyanisole, butylhydroxytoluene, hypophosphorous acid, potassium metabisulfite, propyl, octyl and dodecyl gallate, sodium metabisulfite, sulfur dioxide and tocopherols.

Buffer substances are used to maintain a desired pH of a composition, once established, from the effects of external influences and equilibrium shifts of constituents of the compositions. The buffer substance can be selected from those known to the person skilled in the art of the preparation of pharmaceutical compositions, for example calcium acetate, potassium metaphosphate, potassium dihydrogenphosphate and tartaric acid.

Chelating agents serve to maintain the ionic strength of the pharmaceutical composition; they bind to and thereby effectively remove harmful compounds and metals. These include, for example, dipotassium edetate, disodium edetate and EDTA.

Dermatological active ingredients are added to the pharmaceutical compositions according to the invention where they are to be applied topically; they include, for example, wound healing agents, such as peptide derivatives, yeast, panthenol, hexylresorcinol, phenol, tetracycline hydrochloride, lamin and kinetin; retinoids for the treatment of skin cancer, for example retinol, tretinoin, isotretinoin, etretinate, acitretin and arotinoid, mild antibacterial agents for the treatment of skin infections, for example resorcinol, salicylic acid, benzoyl peroxide, erythromycin-benzoyl peroxide, erythromycin and clindamycin; antifungal agents for the treatment of tinea corporis, tinea ped is, candidiasis and tinea versicolor, for example griseofulvin, azoles, such as miconazole, econazole, itraconazole, fluconazole and ketoconazole, and allylamines, such as naftifine and terfinafine; antiviral agents for the treatment of herpes simplex of the skin, shingles and chickenpox, for example acyclovir, famciclovir and valacyclovir, antihistamines for the treatment of pruritis, atopic and contact dermatitis, for example diphenhydramine, terfenadine, asternizole, loratadine, cetirizine, acrivastine and temelastine, topical anaesthetics for relieving pain, irritation and itching, for example benzocaine, lidocaine, dibucaine and pramoxine hydrochloride, topical analgesics for relieving pain and inflammation, for example methyl salicylate, camphor, menthol and resorcinol, topical antiseptics for the prevention of infection, for example benzalkonium chloride and povidone-iodine, and vitamins and derivatives thereof, such as tocopherol, tocopherol acetate, retinoic acid and retinol.

Dispersing and suspending agents are employed as adjuvants in the preparation of stable formulations and include, for example, poligeenan, povidone and silicon dioxide.

Emollients are preferably non-oily, water-soluble substances which soften and soothe the skin, especially skin that has become dry due to excessive loss of water. Such substances are used with pharmaceutical compositions according to the invention which are intended for topical application; they include, for example, hydrocarbon oils and waxes, triglyceride esters, acetylated monoglycerides, methyl and other alkyl esters of $C_{10}$–$C_{20}$-fatty acids, $C_{10}$–$C_{20}$-fatty acids, $C_{10}$–$C_{20}$-fatty alcohols, lanolin and derivatives, polyhydric alcohol esters, such as polyethylene glycol (200–600), polyoxyethylene sorbitan fatty acid esters, wax esters, phospholipids and sterols; emulsifiers for the preparation of oil-in-water emulsions; excipients, for example laurocapram and polyethylene glycol monomethyl ether, humectants, for example sorbitol, glycerol and hyaluronic acid, ointment bases, for example Vaseline, polyethylene glycol, lanolin and poloxamer, penetration enhancers, for example dimethyl isosorbide, diethyl glycol monoethyl ether, 1-dodecylazacycloheptan-2-one and dimethyl sulfoxide (DMSO); preservatives, for example benzalkonium chloride, benzethonium chloride, alkyl p-hydroxybenzoates, hydantoin derivatives, cetylpyridinium chloride, propylparaben, quarternary ammonium compounds, such as potassium benzoate and thimerosal; sequestering agents, including cyclodextrins, solvents, for example acetone, alcohol, amylene hydrate, butyl alcohol, corn oil, cottonseed oil, ethyl acetate, glycerol, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil and purified water, stabilisers, for example calcium saccharate and thymol, surfactants, for example lapyrium chloride, laureth 4, i.e. α-dodecyl-ω-hydroxy-poly(oxy-1,2-ethanediyl) or polyethylene glycol monododecyl ether.

Emulsifiers, including emulsifying and thickening agents and emulsion aids, are used for the preparation of oil-in-water emulsions if these form the basis of the pharmaceutical compositions according to the invention. These emulsifiers include, for example, non-ionic emulsifiers, such as $C_{10}$–$C_{20}$ fatty alcohols and the products of the condensation of these fatty alcohols with from 2 to 20 mol of ethylene oxide or propylene oxide, the product of the condensation of ($C_6$–$C_{12}$)alkylphenols with from 2 to 20 mol of ethylene oxide, mono- and di-$C_{10}$–$C_{20}$ fatty acid esters of ethylene glycol, $C_{10}$–$C_{20}$ fatty acid monoglyceride, diethylene glycol, polyethylene glycols having an MW of 200–6000, polypropylene glycols having an MW of 200–3000 and in particular sorbitol, sorbitan, polyoxyethylene sorbitol, polyoxyethylene sorbitan, hydrophilic wax esters, cetostearyl alcohol, oleyl alcohol, lanolin alcohols, cholesterol, mono- and diglycerides, glyceryl monostearate, polyethylene glycol monostearate, mixed mono- and distearic esters of ethylene glycol and polyoxyethylene glycol, propylene glycol monostearate and hydroxypropylcellulose. Emulsifiers which contain active amino groups can also be used; these typically include anionic emulsifiers, such as fatty acid soaps, for example sodium, potassium and triethanolamine soaps of $C_{10}$–$C_{20}$ fatty acids, alkali metal, ammonium or substituted ammonium salts of ($C_{10}$–$C_{30}$)alkylsulfate, ($C_{10}$–$C_{30}$)alkylsulfonates and ($C_{10}$–$C_{50}$)alkyl ethoxyether sulfonates. Other suitable emulsifiers include castor oil and hydrogenated castor oil, lecithin; and polymers of 2-propenoic acid together with polymers of acrylic acid, both crosslinked with allyl ethers of sucrose and/or pentaerythritol, having varying viscosities and identified by product names carbomer 910, 934, 934P, 940, 941 and 1342. Cationic emulsifiers which contain active amino groups may also be used, including those based on quaternary ammonium, morpholinium and pyridinium compounds. Similarly, amphoteric emulsifiers which contain active amino groups, such as cocobetaines, lauryldimethylamine oxide and cocoylimidazoline, can be used. Emulsifiers and thickening agents that can be used also include cetyl alcohol and sodium stearate, and emulsion aids, such as oleic acid, stearic acid and stearyl alcohol.

Excipients include, for example, laurocapram and polyethylene glycol monomethyl ether.

If the pharmaceutical composition according to the invention is to be applied topically, penetration enhancers can be used, including, for example, dimethyl isosorbide, diethyl glycol monoethyl ether, 1-dodecylazacycloheptan-2-one and dimethyl sulfoxide (DMSO). Such compositions typically also comprise ointment bases, for example Vaseline, polyethylene glycol, lanolin and poloxamer, which is a polyoxyethylene-polyoxypropylene block copolymer, which may also serve as surfactant or emulsifier.

Preservatives are used to protect pharmaceutical compositions according to the invention against degradation by ambient microorganisms, and include, for example, benzalkonium chloride, benzethonium chloride, alkyl p-hydroxybenzoates, hydantoin derivatives, cetylpyridinium chloride, monothioglycerol, phenol, phenoxyethanol, methylparaben, imidazolidinylurea, sodium dehydroacetate, propylparaben, quaternary ammonium compounds, especially polymers, such as polixetonium chloride, potassium benzoate, sodium formaldehyde sulfoxylate, sodium propionate and thimerosal.

Sequestering agents are used to improve the stability of the pharmaceutical composition according to the invention; they include, for example, the cyclodextrins, which are a family of natural cyclic oligosaccharides which are capable of forming inclusion complexes with a variety of substances and are of varying ring size, those having 6, 7 and 8 glucose radicals per ring usually being referred to as α-cyclodextrins, β-cyclodextrins and γ-cyclodextrins, respectively. Suitable cyclodextrins include, for example, α-cyclodextrin, β-cyclodextrin, γ-cyclodextrin, δ-cyclodextrin and cationised cyclodextrins.

Solvents which can be used in the preparation of the pharmaceutical compositions according to the invention include, for example, acetone, alcohol, amylene hydrate, butyl alcohol, corn oil, cottonseed oil, ethyl acetate, glycerol, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil and purified water.

Stabilisers which are suitable for use include, for example, calcium saccharate and thymol.

Thickening agents are typically used in formulations for topical application in order to provide these with the desired viscosity and the desired handling properties; they include, for example, cetyl ester wax, myristyl alcohol, paraffin, synthetic paraffin, emulsifying wax, microcrystalline wax, bleached wax and yellow wax.

Sugars are frequently used to provide the pharmaceutical compositions according to the invention with various desired properties and to improve the results achieved; they include, for example, monosaccharides, disaccharides and polysaccharides, such as glucose, xylose, fructose, reose, ribose, pentose, arabinose, allose, tallose, altrose, mannose, galactose, lactose, sucrose, erythrose, glyceraldehyde, or any combinations thereof.

Surfactants are used to provide multi-component pharmaceutical compositions according to the invention with stability, to enhance existing properties of these compositions, and to provide the compositions with new desired properties. Surfactants are used as wetting agents, antifoams, for reducing the surface tension of water, and as emulsifiers, dispersants and penetration enhancers; they include, for example, lapyrium chloride; laureth 4, i.e. α-dodecyl-ω-hydroxypoly(oxy-1,2-ethanediyl) or polyethylene glycol monododecyl ether, laureth 9, i.e. a mixture of polyethylene glycol monododecyl ethers having an average of 9 ethylene oxide groups per molecule, monoethanolamine, nonoxynol 4, 9 and 10, i.e. polyethylene glycol mono(p-nonylphenyl) ether, nonoxynol 15, i.e. α-(p-nonylphenyl)-ω-hydroxypentadeca(oxyethylene), nonoxynol 30, i.e. α-(p-nonylphenyl)-ω-hydroxytriaconta(oxyethylene), poloxalene, i.e. nonionic polymer of the polyethylenepolypropylene glycol type, MW=approx. 3000, poloxamer, referred to above in the discussion of ointment bases, polyoxyl (8), (40) and (50) stearate, i.e. poly(oxy-1,2-ethanediyl), α-hydro-ω-hydroxyoctadecanoate, polyoxyl 10 oleyl ether, i.e. poly(oxy-1,2-ethanediyl), α-[(Z)-9-octadecenyl-ω-hydroxy-, polysorbate 20, i.e. sorbitan, monododecanoate, poly(oxy-1,2-ethanediyl), polysorbate 40, i.e. sorbitan, monohexadecanoate, poly(oxy-1,2-ethanediyl), polysorbate 60, i.e. sorbitan, monooctadecanoate, poly(oxy-1,2-ethanediyl), polysorbate 65, i.e. sorbitan, trioctadecanoate, poly(oxy-1,2-ethanediyl), polysorbate 80, i.e. sorbitan, mono-9-octadecenoate, poly(oxy-1,2-ethanediyl), polysorbate 85, i.e. sorbitan, tri-9-octadecenoate, poly(oxy-1,2-ethanediyl), sodium lauryl sulfate, sorbitan monolaurate, sorbitan monooleate, sorbitan monopalmitate, sorbitan monostearate, sorbitan sesquioleate, sorbitan trioleate and sorbitan tristearate.

The pharmaceutical compositions according to the invention are prepared in an extremely simple manner as is well known to the average person skilled in the art. If the pharmaceutical compositions according to the invention are simple aqueous solutions or solutions in other solvents, the various constituents of the overall composition are combined in any desired practical sequence, which is determined principally by considerations of convenience. The constituents that have lower solubility in water, but adequate solubility in the same auxiliary solvent with water, can all be dissolved in this auxiliary solvent, after which the auxiliary solution is added to the water content of the excipient, causing the substances dissolved therein to dissolve in the water. To support this dispersion process or dissolution process, a surfactant can be employed.

If the pharmaceutical compositions according to the invention are to be in the form of emulsions, the constituents of the pharmaceutical composition are combined in accordance with the following general procedures. The continuous water phase is firstly heated to a temperature in the range from about 60° C. to about 95° C., preferably from about 70° C. to about 95° C., with the choice of temperature used depending on the physical and chemical properties of the constituents which form the oil-in-water emulsion. As soon as the continuous water phase has reached the selected temperature, the constituents of the final composition which are to be added at this stage are mixed with the water with vigorous stirring and dispersed therein. Next, the temperature of the water is restored approximately to the initial level, after which the constituents of the composition which form the next step are added to the composition mixture with moderate stirring, and mixing is continued for from about 5 to about 60 minutes, preferably from about 10 to about 30 minutes, depending on the constituents of the first two steps. The composition mixture is then passively or actively cooled to from about 20° C. to about 55° C. in order that further components can be added in the remaining steps, after which sufficient water is added that the originally determined concentration in the overall composition is reached.

In accordance with the present invention, the pharmaceutical compositions can be in the form of a sterile injection preparation, for example a sterile aqueous or oil-based suspension for injection. This suspension can be formulated in accordance with techniques known in the art using suitable dispersants, wetting agents and suspension media. The sterile injection preparation can also be a sterile solution or suspension for injection in a non-toxic parenterally acceptable diluent or solvent, for example in the form of a solution in 1,3-butanediol. Acceptable constituents and solvents which can be used include water, Ringer's solution and isotonic saline solution. In addition, sterile stabilised oils are usually used as solvent or suspension medium. For this purpose, any mild stabilised oil, including synthetic mono- or diglycerides, can be used. Fatty acids, such as oleic acid and its glyceride derivatives, are suitable for the preparation of injectables, as are natural pharmaceutically acceptable oils, such as olive oil or castor oil, in particular in the form of their polyethoxylates. These oil solutions or suspensions can also contain a long-chain alcohol, such as RH, HClX or a similar alcohol, as diluent or dispersant.

The pharmaceutical compositions according to the invention can be administered orally in any orally acceptable dosage form, including, but not limited to, capsules, tablets, aqueous suspensions or solutions. In the case of oral tablets, excipients which are frequently used include lactose and corn starch. Lubricants, such as magnesium stearate, are also typically added. In the case of oral administration in capsule form, useful diluents include lactose and dried corn starch. If aqueous solutions are to be used orally, the active ingredient is combined with emulsifiers and suspension media. If desired, certain sweeteners, flavours or dyes can also be added. However, the pharmaceutical compositions according to the invention can also be administered in the form of suppositories for rectal administration. Such suppositories can be produced by mixing the agent with a suitable non-irritating excipient which is solid at room temperature, but liquid at the rectal temperature and therefore melts in the rectum and thus releases the medicament. These substances include cocoa butter, beeswax and polyethylene glycols.

The pharmaceutical compositions according to the invention can also be administered topically, in particular if areas or organs that are readily accessible by topical application form the target of treatment, including eye diseases, skin diseases, or diseases of the lower digestive tract. Suitable topical formulations can easily be prepared for these areas or organs.

Topical application for the lower intestinal tract can be effected as a rectal suppository formulation, as described above, or in the form of a suitable enema formulation. Topically active transdermal patches can likewise be used.

For topical application, the pharmaceutical compositions can be formulated as a suitable ointment comprising the active constituent suspended or dissolved in one or more excipients. Excipients for topical administration of the compounds according to the invention include, but are not limited to, mineral oil, paraffin oil, white Vaseline, propylene glycol, polyoxyethylene-polyoxypropylene compound, emulsifying wax and water. However, the pharmaceutical compositions can also be formulated as a suitable lotion or cream comprising the active constituents suspended or dissolved in one or more pharmaceutically acceptable excipients. Suitable excipients include, but are not limited to, mineral oil, sorbitan monostearate, polysorbate, cetyl ester wax, cetearyl alcohol, 2-octyldodecanol, benzyl alcohol and water.

Pharmaceutical compositions to which the present compound extends also include those in which the therapeutically effective amount of an active ingredient comprising a compound of the formula I which is required for the treatment or prevention of diseases, pathological disorders and conditions which are mediated by or associated with modulation of PDE IV activity as described herein is provided in a dosage form which is suitable for systemic administration. A pharmaceutical composition of this type comprises the active ingredient in a suitable liquid form for delivery by: (1) injection or infusion, be it intraarterially, intra- or transdermally, subcutaneously, intramuscularly, intraspinally, intrathecally or intravenously, where the active ingredient (a) is in the form of a dissolved substance in solution, (b) is present in the discontinuous phase of an emulsion or in the discontinuous phase of an emulsion with phase reversal, in which the phase inverts on injection or infusion, where emulsions of this type comprise suitable emulsifiers, or (c) is present as a suspended solid in colloidal or microparticulate form in a suspension, where this suspension comprises suitable suspension media, (2) injection or infusion into suitable body tissues or cavities as a depot, where the composition stores the active ingredient and subsequently releases it for systemic distribution in the form of a delayed release, sustained release or controlled release, (3) instillation, inhalation or insufflation of the pharmaceutical composition in a suitable solid form into suitable body tissues or cavities, where the active ingredient (a) is present in a solid implant of the composition which ensures release of the active ingredient in the form of delayed release, sustained release or controlled release, (b) is present in a particulate composition which is inhaled into the lungs, or (c) is present in a particulate composition which is blown into suitable body tissues or cavities, where the composition is, if desired, ready for the release of the active ingredient in the form of delayed release, sustained release or controlled release, or (4) ingestion of the pharmaceutical composition in a suitable solid or liquid form for peroral delivery of the active ingredient, where the active ingredient is present in a solid dosage form, or (b) is present in a liquid dosage form.

Individual dosage forms of the above-described pharmaceutical compositions include (1) suppositories as a special type of implant, comprising bases which are solid at room temperature, but melt at body temperature and thus slowly release the active ingredient they contain into the surrounding body tissue, where the active ingredient is absorbed and transported to effect systemic administration, (2) solid peroral dosage forms selected from the group consisting of (a) delayed-release oral tablets, capsules, caplets, lozenges, troches and multiparticulates, (b) enteric-coated tablets and capsules which prevent release and absorption in the stomach and thus enable delivery distal to the stomach of the patient being treated, (c) sustained-release oral tablets, capsules and microparticulates which provide systemic release of the active ingredient in a controlled manner over a period of up to 24 hours, (d) fast-disintegrating tablets, (e) encapsulated solutions, (f) oral pastes, (g) granules incorporated into the food of a patient being treated, and (h) liquid peroral dosage forms selected from the group consisting of solutions, suspensions, emulsions, inverse emulsions, elixirs, extracts, tinctures and concentrates.

Pharmaceutical compositions to which the present compound extends also include those in which the therapeutically effective amount of an active ingredient comprising a compound according to the invention which is required for the treatment or prevention of diseases, pathological disorders and conditions which are mediated by or associated with modulation of PDE IV activity as described herein is provided in a dosage form which is suitable for local administration to a patient being treated, where a pharmaceutical composition of this type comprises the active ingredient in a suitable liquid form for delivery of the active ingredient by (1) local injection or infusion, be it intraarterially, intraarticularly, intrachondrially, intracostally, intracysticly, intra- or transdermally, intrafascicularly, intraligamentously, intramedullarly, intramuscularly, intranasally, intraneurally, intraocularly, i.e. ophthalmic administration, intraosteally, intrapelvicly, intrapericardially, intraspinally, intrasternally, intrasynovially, intratarsally or intrathecally, also including constituents which ensure delayed release, controlled release or sustained release of the active ingredient into this local site; where the active ingredient (a) is in the form of a dissolved substance in solution, (b) is present in the discontinuous phase of an emulsion or in the discontinuous phase of an emulsion with phase reversal, in which the phase inverts on injection or infusion, where emulsions of this type comprise suitable emulsifiers, or (c) is present as a suspended solid in colloidal or microparticulate form in a suspension, where this suspension comprises suitable suspension media, or (2) is in the form of an injection or infusion as a depot for release of the active ingredient at the local site, where the composition stores the active ingredient and subsequently releases it to the local site in the form of delayed release, sustained release or controlled release, where the composition also comprises constituents which ensure that the active ingredient primarily acts locally and causes little systemic carryover, or where the pharmaceutical composition comprises the active ingredient in a suitable solid form for delivery of the inhibitor by the following method: (3) instillation, inhalation or insufflation at this local site, where the active ingredient is present in: (a) a solid implant of the composition which is implanted at this local site, where the composition releases the active ingredient to the said local site optionally in the form of delayed release, sustained release or controlled release, (b) in a particulate composition which is inhaled into a local site, also including the lungs, or (c) in a particulate composition which is blown into a local site, where the composition comprises constituents which ensure that the active ingredient primarily acts locally, with insignificant systemic carryover, and optionally releases the active ingredient locally in the form of delayed release, sustained release or controlled release. For ophthalmic use, the pharmaceutical compositions can be formulated as micronised suspension in isotonic, pH adjusted sterile saline solution, or, preferably, as solutions in isotonic, pH adjusted sterile saline solution, with or without preservatives, such as benzylalkonium chloride. Alternatively, for ophthalmic use, the pharmaceutical compositions can be formulated in an ointment, such as Vaseline.

The pharmaceutical compositions according to the invention can also be administered by nasal aerosol or inhalation using a nebuliser, dry powder inhaler or dispensing inhaler. Such compositions are prepared by techniques which are well known in pharmaceutical formulation and can be prepared in the form of solutions in saline solution with benzyl alcohol or other suitable preservatives, absorption promoters for improving bioavailability, fluorohydrocarbons and/or other conventional solubilising agents or dispersants.

As already mentioned, the compounds of the formula I according to the invention can be administered systemically to a patient to be treated in the form of a pharmaceutical composition in a suitable liquid form by injection or infusion. There are various sites and organ systems in the body of the patient which will allow the correctly formulated pharmaceutical composition, as soon as it has been injected or infused, to permeate the entire body and all organ systems of the patient being treated. An injection is a single dose of the pharmaceutical composition forced, usually by means of a syringe, into the relevant tissue. The most frequent types of injection are intramuscular, intravenous and subcutaneous. By contrast, an infusion is the gradual introduction of the pharmaceutical composition into the relevant tissue. The most frequent type of infusion is intravenous. Other types of injection or infusion include intraarterial, intra- or transdermal (including subcutaneous), or intraspinal, in particular intrathecal. In these liquid pharmaceutical compositions, the active ingredient may be in the form of a dissolved substance in solution. This is the commonest and most preferred type of such a composition, but requires an active ingredient in a salt form that has reasonably good solubility in water. Water (or saline solution) is by far the most preferred solvent for such compositions. Occasionally supersaturated solutions can be used, but these present stability problems and are therefore impractical for everyday use.

If it is not possible to obtain a preferred compound in a form which has the requisite solubility in water, as is sometimes the case, it is within the skill of the average person skilled in the art to prepare an emulsion, which is a dispersion of small droplets of a liquid, the discontinuous or internal phase, in a second liquid, the continuous or external phase, with which it is immiscible. The two liquids are kept in the emulsified state by pharmaceutically acceptable emulsifiers. If the active ingredient is a water-in-soluble oil, it can therefore be administered in an emulsion in which it forms the discontinuous phase. If the active ingredient is water-insoluble, but can be dissolved in a water-immiscible solvent, an emulsion can likewise be used. Although the active ingredient would most frequently be used as the discontinuous or internal phase of a so-called oil-in-water emulsion, it could also be used as the discontinuous or internal phase of an emulsion with phase reversal, which is usually referred to as a water-in-oil emulsion. Here, the active ingredient is soluble in water and could be administered as a simple aqueous solution. However, emulsions of this type with phase reversal reverse on injection or infusion into an aqueous medium, such as the blood, and offer the advantage of faster and more efficient dispersion of the active ingredient into this aqueous medium than on use of an aqueous solution. Emulsions with phase reversal are prepared using suitable pharmaceutically acceptable emulsifiers that are known in the art.

If the active ingredient has limited water solubility, it can also be administered as a suspended solid in colloidal or finely divided form in a suspension prepared using suitable pharmaceutically acceptable suspension media. The suspended solids comprising the active ingredient may also be formulated as delayed release, sustained release or controlled release compositions.

Although systemic administration is most frequently carried out by injection or infusion of a liquid, there are many situations in which it is advantageous or even necessary to deliver the active ingredient as a solid. Systemic administration of solids is carried out by instillation, inhalation or insufflation of a pharmaceutical composition in a suitable solid form comprising the active ingredient. Instillation of the active ingredient may entail inserting a solid implant of the composition into suitable body tissues or cavities. The implant may comprise a matrix of biocompatible and biodegradable substances in which particles of a solid active ingredient are dispersed, or in which droplets or isolated cells of a liquid active ingredient may possibly be included. The matrix should wherever possible be broken down and completely absorbed by the body. The composition of the matrix is also preferably selected so as to provide controlled release, sustained release or delayed release of the active ingredient over extended periods of time, even several months.

The term "implant" usually refers to a solid pharmaceutical composition comprising the active ingredient, while the term "depot" usually denotes a liquid pharmaceutical composition comprising the active ingredient, which is deposited in any suitable body tissue or any suitable body cavity and thus forms a reservoir or pool which slowly migrates into the surrounding tissue and organs and finally and eventually is systemically distributed. However, these distinctions are not always handled strictly in the art, and it is therefore intended that the scope of the present invention also extends to liquid implants and solid depots, and even solid and liquid mixed forms in each case. Suppositories can be regarded as a type of implant, since they comprise bases which are solid at room temperature, but melt at a patient's body temperature and thus slowly release the active ingredient with which they are provided into the surrounding tissue of the patient's body, where the active ingredient is absorbed and transported away and is thus administered systemically.

Systemic administration can also be carried out by inhalation or insufflation of a powder, i.e. a particulate composition comprising the active ingredient. For example, the active ingredient in powder form may be inhaled into the lungs using conventional devices for aerosol formation of particulate formulations. The active ingredient as a particulate formulation can also be administered by insufflation, i.e. blown or otherwise dispersed into suitable body tissues or cavities by simple dusting or using conventional devices for aerosol formation of particulate formulations. These particulate compositions can likewise be formulated in accordance with well-known principles and with known materials to give an active ingredient with delayed release, sustained release or controlled release.

Other means of systemic administration, in which the active ingredients according to the invention are used either in liquid or solid form, include the transdermal, intranasal and ophthalmic methods of administration. In particular, transdermal patches can be produced by techniques known in medicament delivery and applied to the skin of the patient to be treated, after which the active ingredient, owing to its formulated solubility properties, migrates through the epidermis and into the dermal layers of the patient's skin, where it is taken up as part of the general circulation of the patient and finally and ultimately results in systemic distribution of the active ingredient over a desired, extended period of time. These also include implants which are placed beneath the epidermal layer of the skin, i.e. between the epidermis and the dermis of the skin of the patient being treated. Such an implant is formulated in accordance with well-known principles and materials which are frequently used in this delivery technique, and can be produced in such a way that the active ingredient is delivered into the systemic circulation of the patient in accordance with the principle of controlled release, sustained release or delayed release. Subepidermal (subcuticular) implants of this type can be used just as easily as transdermal patches and offer the same effective delivery, but without being subjected to the degradation, damage or accidental removal as a consequence of the patch being exposed on the outermost layer of the patient's skin.

In the above description of pharmaceutical compositions comprising a preferred compound, the equivalent expressions "administration", "administration of", "administering" and "administer a" have been used with respect to these pharmaceutical compositions. In the present connection, these expressions are intended to mean that a patient in need of treatment is provided with a pharmaceutical composition according to the invention by any of the methods of administration described here, where the active ingredient is a preferred compound or a prodrug, a derivative or a metabolite thereof which is suitable for the treatment of a disease, pathological disorder or condition which is mediated by or associated with modulation of PDE IV activity in this patient. The present invention therefore extends to any other compound which, on administration to a patient, is capable of directly or indirectly making a preferred compound available. Such compounds are known as prodrugs, and a large number of established procedures exist for the preparation of such prodrug forms of the preferred compounds.

The dose or dosage of the for the treatment or prevention of a disease, pathological disorder or condition which is mediated by or associated with modulation of PDE IV activity depends on a variety of factors, such as the nature of the inhibitor, the size of the patient, the aim of the treatment, the nature of the pathology to be treated, the pharmaceutical composition used in each case and the observations and conclusions of the treating physician.

In the case of an oral dosage form, for example a tablet or capsule, suitable doses of the compounds of the formula I are between about 0.1 μg of active ingredient/kg and about 50.0 mg of active ingredient/kg of body weight per day, preferably between about 5.0 μg of active ingredient/kg and about 5.0 mg of active ingredient/kg of body weight per day, more preferably between about 10.0 μg of active ingredient/kg and about 1.0 mg of active ingredient/kg of body weight per day, most preferably between about 20.0 μg of active ingredient/kg and about 0.5 mg of active ingredient/kg of body weight per day.

If the dosage form is administered topically to the bronchia and lungs, for example by means of a powder inhaler or nebuliser, suitable doses of the compounds are between about 0.001 μg of active ingredient/kg and about 10.0 mg of active ingredient/kg of body weight per day, preferably between about 0.5 μg of active ingredient/kg and about 0.5 mg of active ingredient/kg of body weight per day, more preferably between 1.0 μg of active ingredient/kg and about 0.1 mg of active ingredient/kg of body weight per day, most preferably between about 2.0 μg of active ingredient/kg and about 0.05 mg of active ingredient/kg of body weight per day.

In order to explain the range of the daily oral dose that could be used as described above and with the aid of a typical body weight of 10 kg and 100 kg, suitable doses of the compounds of the formula I are between about 1.0–10.0 μg and 500.0–5000.0 mg of the active ingredient comprising a preferred compound per day, preferably between about 50.0 and 500.0 μg and 50.0–500.0 mg of the active ingredient comprising a preferred compound per day, more preferably between about 100.0–1000.0 μg and 10.0–100.0 mg of an active ingredient comprising a preferred compound per day, most preferably between about 200.0–20,000 μg and about 5.0–500 mg of the active ingredient comprising a preferred compound per day. These dosage ranges represent total doses of the active ingredient per day for a particular patient. The number of times per day that a dose is administered depends on pharmacological and pharmacokinetic factors, such as the half-life of the active ingredient, which reflects its rate of catabolism and clearance, as well as the minimum and optimum blood plasma level or other body fluid levels of the active ingredient in a patient that are necessary for therapeutic efficacy.

When determining the number of doses per day and the amount of active ingredient per dose that will be administered, numerous other factors must also be considered. Another such factor is not least the particular response of the patient being treated. Thus, for example, if the active ingredient is used for the treatment or prevention of asthma on topical administration via aerosol inhalation into the lungs, from one to four doses consisting of actuations of a dispensing device, i.e. "puffs" of an inhaler, are administered per day, each dose comprising from about 50.0 μg to about 10.0 mg of active ingredient.

The invention furthermore also relates to medicaments comprising at least one compound of the formula I and/or pharmaceutically usable derivatives, solvates and stereoisomers thereof, mixtures thereof in all ratios, and, if desired, excipients and/or adjuvants.

The invention furthermore also relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, and mixtures thereof in all ratios, and (b) an effective amount of a further medicament active ingredient.

The set comprises suitable containers, such as boxes, individual bottles, bags or ampoules. The set may, for example, comprise individual ampoules each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

All temperatures above and below are given in ° C. In the examples which follow, "conventional work-up" means: water is added if necessary, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation:

Mass spectrometry (MS) (electron impact ionisation) M$^+$

FAB (fast atom bombardment)(M+H)$^+$

EXAMPLE 1

1.1 3.5 ml of chloroacetyl chloride are added dropwise with stirring and cooling to a solution of 9.8 g of (1) and 3.8 ml of pyridine in 100 ml of dichloromethane (DCM), and the mixture is stirred at room temperature for a further 16 hours. Conventional work-up gives 6.1 g of

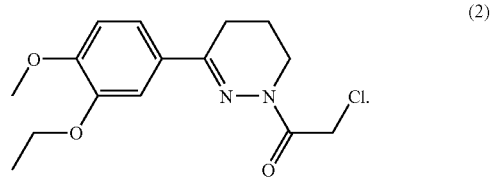

1.2 5.8 g of (2) are added to a solution of 3.045 g of N-hydroxyphthalimide and 3.3 g of potassium carbonate in 35 ml of 1-methyl-2-pyrrolidone (NMP), and the mixture is stirred at 50° for a further 4 hours. Conventional work-up gives 4.8 g of (3).

1.3 700 mg of ethanolamine are added to a solution of 4.8 g of (3) in 200 ml of ethyl acetate, and the mixture is stirred at 60° for 2 hours. Conventional work-up gives 2.8 g of (4).

1.4 44.3 mg of 4-methoxybenzaldehyde are added to a solution of 0.1 g of (4) and 0.02 ml of glacial acetic acid in 10 ml of ethanol, and the mixture is stirred at room temperature for 16 hours.

The solvent is removed, and the residue is stirred up with ether, filtered off with suction and washed with ether, giving 110 mg of the compound 4-methoxybenzaldehyde O-{2-[3-(3-ethoxy-4-methoxyphenyl)-5,6-dihydro-4H-pyridazin-1-yl]-2-oxoethyl}oxime (I-A-1; see Table 1).

Compounds of the formulae I-A, I-B and I-C

TABLE 1

I-A, I-B, I-C

| No. | R¹ | R² | R³ | B | Notes |
|---|---|---|---|---|---|
| I-A-1 | OMe | OEt | H | 4-Methoxyphenyl | |
| I-A-2 | OMe | OEt | H | Phenyl | |
| I-A-3 | OMe | OEt | H | 4-Hydroxyphenyl | |
| I-A-4 | OMe | OEt | H | Pyridin-4-yl | |
| I-A-5 | OMe | OEt | H | Pyridin-4-yl N-oxide | |
| I-B-1 | OMe | OPr | H | 4-Methoxyphenyl | |
| I-B-2 | OMe | OPr | H | Phenyl | |
| I-B-3 | OMe | OPr | H | Pyridin-4-yl | |
| I-B-4 | OMe | OPr | H | Pyridin-4-yl N-oxide | |
| I-B-5 | OMe | OPr | H | 4-Nitrophenyl | |
| I-C-1 | OMe | OEt | H | 4-BOC-aminophenyl | |
| I-C-2 | OMe | OEt | H | 4-Aminophenyl | |
| I-C-3 | OMe | OEt | H | 4-[(CN)₂C=N—NH]-phenyl | |
| I-C-4 | OMe | OEt | H | 3-[(CN)₂C=N—NH]-phenyl | |
| I-C-5 | OMe | OPr | H | 4-[(CN)₂C=N—NH]-phenyl | |

Me = methyl; Et = ethyl; Pr = propyl

Analogous reaction of (4) with
benzaldehyde,
4-hydroxybenzaldehyde,
pyridine-4-carbaldehyde,
pyridine N-oxide 4-carbaldehyde, gives the following compounds:
I-A-2,
I-A-3,
I-A-4,
I-A-5.

EXAMPLE 2

Analogously to Example 1, reaction of

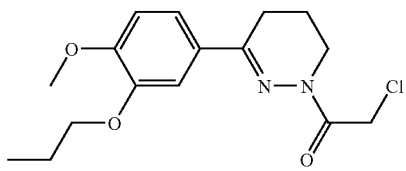

(5)

with
4-methoxybenzaldehyde,
benzaldehyde,
pyridine-4-carbaldehyde,
pyridine N-oxide 4-carbaldehyde,
4-nitrobenzaldehyde gives the following compounds of the formula I-B (Table 1):
I-B-1,
I-B-2,
I-B-3,
I-B-4,
I-B-5.

EXAMPLE 3

3.1 Analogously to Example 1, reaction of (4) with 4-BOC-aminobenzaldehyde gives the compound I-C-1 (Table 1).

3.2 Removal of the BOC protecting group using HCl in dioxane gives I-C-2.

3.3 270 mg of I-C-2 are added to a solution of 0.6 ml of 25% HCl in 10 ml of water. The mixture is cooled to −2°, 48.3 mg of NaNO₂ are added, and the mixture is stirred for a further 1 hour. 43.5 mg of malononitrile are then added, and the mixture is stirred at room temperature for a further 1 hour. The mixture is adjusted to pH 5 using saturated sodium acetate solution, and the precipitated material is filtered off, washed with water and dried at 50° for 16 hours.

The equimolar amount of 0.5 N KOH in methanol is added to the filtrate, and the mixture is evaporated. The residue is recrystallised from ethanol. Yield: 230 mg of 2-{[4-({2-[3-(3-ethoxy-4-methoxyphenyl)-5,6-dihydro-4H-pyridazin-1-yl]-2-oxoethoxyimino}methyl)phenyl]hydrazono}malononitrile, potassium salt (I-C-3)

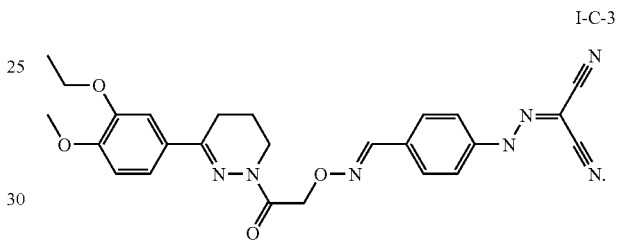

I-C-3

The following compounds are obtained analogously:
2-{[3-({2-[3-(3-ethoxy-4-methoxyphenyl)-5,6-dihydro-4H-pyridazin-1-yl]-2-oxoethoxyimino}methyl)phenyl]hydrazono}malononitrile, potassium salt (I-C-4) and
2-{[3-({2-[3-(3-propoxy-4-methoxyphenyl)-5,6-dihydro-4H-pyridazin-1-yl]-2-oxoethoxyimino}methyl)phenyl]hydrazono}malononitrile, potassium salt (I-C-5).

EXAMPLE 4

4.1 293 mg of benzoylformic acid are added to a solution of 600 mg of (4) in ethanol/glacial acetic acid, and the mixture is stirred at room temperature for 16 hours. The solvent is distilled off, and the residue is stirred up with ether, filtered off with suction and washed with ether, giving 800 mg of the compound {2-[3-(3-ethoxy-4-methoxyphenyl)-5,6-dihydro-4H-pyridazin-1-yl]-2-oxoethoxyimino}-2-phenylacetic acid (I-D-1; Table 2).

Compounds of the formula I-D

TABLE 2

I-D

| No. | R¹ | R² | R³ | B | Notes |
|---|---|---|---|---|---|
| I-D-1 | OMe | OEt | COOH | Phenyl | |
| I-D-2 | OMe | OEt | N-(1-Methylpiperidin-4-yl)-N-methylamino- | Phenyl | |

TABLE 2-continued

I-D

| No. | R¹ | R² | R³ | B | Notes |
|---|---|---|---|---|---|
| I-D-3 | OMe | OEt | 4-Methylpiperazinyl-carbonyl | Phenyl | |
| I-D-4 | OMe | OEt | N,N-Dimethylamino-ethylaminocarbonyl | Phenyl | |

Me = methyl; Et = ethyl; Pr = propyl 4.2 Further reaction of I-D-1 with the amines 1-methyl-4-(methylamino)piperidine, 4-methylpiperazine, 2-dimethylaminoethylamine gives the following compounds:

2-{2-[3-(3-ethoxy-4-methoxyphenyl)-5,6-dihydro-4H-pyridazin-1-yl]-2-oxoethoxyimino}-N-methyl-N-(1-methylpiperidin-4-yl)-2-phenylacetamide (I-D-2)

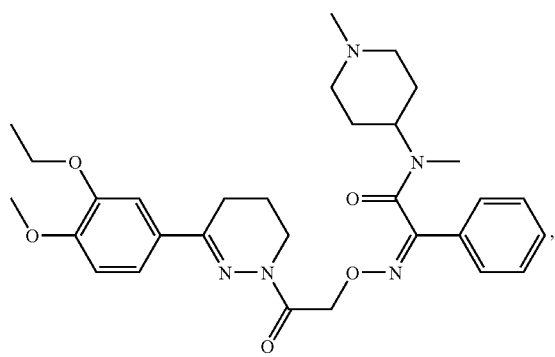

1-(4-methylpiperazin-1-yl)-2-phenylethane-1,2-dione 2-(O-{2-[3-(3-ethoxy-4-methoxyphenyl)-5,6-dihydro-4H-pyridazin-1-yl]-2-oxoethyl}oxime (I-D-3)

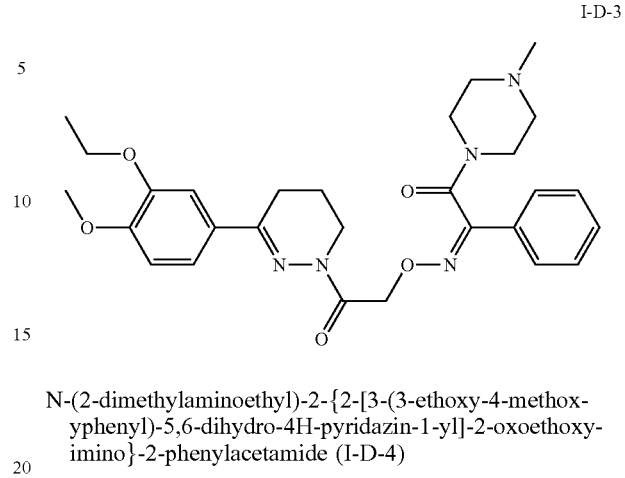

N-(2-dimethylaminoethyl)-2-{2-[3-(3-ethoxy-4-methoxyphenyl)-5,6-dihydro-4H-pyridazin-1-yl]-2-oxoethoxyimino}-2-phenylacetamide (I-D-4)

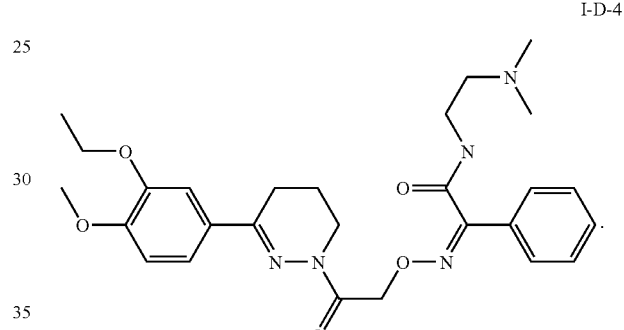

EXAMPLE 5

A solution of 500 mg of I-C-3, 66 mg of ammonium chloride, 81 mg of sodium azide and a catalytic amount of lithium chloride in 4 ml of DMF is stirred at 120° for 24 hours. The work-up is carried out in a conventional manner, after which the dried crystals are re-dissolved in methanol. An equivalent amount of KOH in methanol is added. The solvent is removed, and ethyl acetate/diethyl ether is added to the residue.

Yield: 460 mg of the compound 2-{[4-({2-[3-(3-ethoxy-4-methoxyphenyl)-5,6-dihydro-4H-pyridazin-1-yl]-2-oxoethoxyimino}methyl)phenyl]hydrazono}-2-(1H-tetrazol-5-yl)acetonitrile, potassium salt (I-E-1)

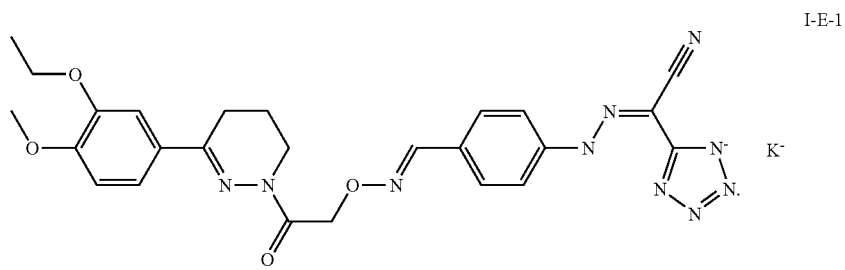

EXAMPLE I

Effect of the Compounds of the Formula I on the Proliferation of T-Cells

Peripheral blood monocytes (PBMCs) are isolated from the blood of healthy donors by the Lymphoprep gradient method. In each well, 200,000 PBMCs are cultivated in RPMI1640 culture medium with 5% of heat-deactivated human serum (AB pool) for 5 days at 37° C. and 10% $CO_2$ in 96-well flat-base microtitre plates. The T-cells of the PBMC sample are stimulated selectively against CD3 with a monoclonal antibody. The cultures are prepared in triplicate, including a control group without treatment.

The compounds of the formula I are dissolved in DMSO in a concentration of $10^{-2}$ M and diluted with culture medium. The control cultures are treated with DMSO corresponding to the inhibitor concentration. $^3$H-hymidine is added to the cultures 18 hours before the end of the assay. The uptake of the radioactivity into the cells is then measured using a beta counter. The values of at least three independent experiments are calculated as percentage inhibition of the control (mean±SFN) without inhibitor. The $IC_{50}$ value is determined from these values.

EXAMPLE II

Effect of the Compounds of the Formula I on Cytokine Production in Human Peripheral Blood Monocytes Peripheral blood monocytes (PBMCs) are isolated from the blood of healthy donors by the Lymphoprep gradient method. In each well, 200,000 PBMCs are cultivated in RPMI1640 culture medium with 5% of heat-deactivated human serum (AB pool) at 37° C. and 10% $CO_2$ in 96-well flat-base microtitre plates. The cultures are prepared in triplicate, including a control group. Solutions of the compounds of the formula I in DMSO are prepared in a concentration of $10^{-2}$ M and diluted with culture medium.

The control cultures are treated with DMSO concentrations corresponding to the inhibitor concentrations.

The culture supernatants from three independent experiments are pooled, and the cytokine activity in the supernatant is measured using commercially available ELISA test kits.

The data are calculated as percentage inhibition/stimulation of the control without the compound, and the $IC_{50}$ value or $EC_{50}$ value during the stimulation is determined therefrom.

The example below relate to pharmaceutical preparations:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced in a conventional manner into hard gelatine capsules in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound of the formula I:

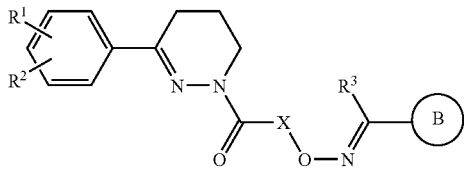

in which:
R¹, R² are each, independently of one another, H, OH, OR⁸, —SR⁸, —SOR⁸, —SO₂R⁸ or Hal, or
R¹ and R² together are alternatively —OCH₂O— or —OCH₂CH₂O—;
R³ is H, A"R⁷, COA"R⁷, COOA"R⁷, CONH₂, CONHA"R⁷, CON(A"R⁷)(A"'R⁷), CONR¹⁰Het, NH₂, NHA"R⁷, N(A"R⁷)(A"'R⁷), NCOA"R⁷ or NCOOA"R⁷;
B is an aromatic isocyclic or heterocyclic radical, which may be unsubstituted or monosubstituted, disubstituted or trisubstituted by R⁴, R⁵ and/or R⁶;
X is alkylene having 1–10 carbon atoms or alkenylene having 2–8 carbon atoms, in which one, two or three CH₂ groups are optionally replaced by O, S, SO, SO², NH or NA"R⁷, and 1–7 H atoms are optionally replaced by F and/or Cl;
R⁴, R⁵, R⁶ are each, independently of one another, H, A"R⁷, OH, OA"R⁷, NO², NH₂, NHA"R⁷, N(A"R⁷)(A"'R⁷), NHCOA"R⁷, NHCOOA"R⁷, NHCONH₂, NHCONHA"R⁷, NHCON(A"R⁷)(A"'R⁷), Hal, COOH, COOA"R⁷, CONH₂, CONHA"R⁷, CON(A"R⁷)(A"R⁷),

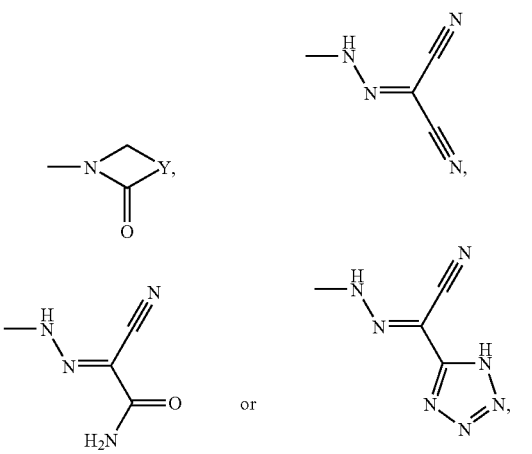

R⁷ is H, COGH, COGA, CONH₂, CONHA, CONAA', NH₂, NHA, NAA', NCOA, NCOOA, OH or OA;
R⁸ is A, cycloalkyl having 3–7 carbon atoms, alkylenecycloalkyl having 4–8 carbon atoms or alkenyl having 2–8 carbon atoms;
R⁹ is alkyl having 1–10 carbon atoms, cycloalkyl having 3–7 carbon atoms, alkylenecycloalkyl having 4–8 carbon atoms or alkenyl having 2–8 carbon atoms, in which one, two or three CH₂ groups are optionally replaced by O, S, SO, SO₂, NH, NMe, NEt and/or by CH=CH— groups, 1–7H atoms are optionally replaced by F and/or Cl, and/or 1H atom is optionally replaced by R⁷, Y is alkylene having 1–10 carbon atoms or alkenylene having 2–8 carbon atoms, in which one, two or three CH₂ groups are optionally replaced by O, S, SO, SO₂, NH or NR⁹ and/or 1–7H atoms are optionally replaced by F and/or Cl;
A, A' are each, independently of one another, aryl, Het, alkyl having 1–10 carbon atoms or alkenyl having 2–8 carbon atoms, in which one, two or three CH₂ groups are optionally replaced by O,S, SO, SO₂, NH or NR⁹ and/or 1–7 H atoms may be replaced by F and/or Cl, or
A and A' together are alternatively an alkylene chain having 2–7 carbon atoms, in which one, two or three CH₂ groups are optionally replaced by O, S, SO, SO₂, NH, NR⁹, NCOR⁹ or NCOOR⁹;
A", A"' are each, independently of one another, a single bond, alkylene having 1–10 carbon atoms, alkenylene having 2–8 carbon atoms or cycloalkylene having 3–7 carbon atoms, in which one, two or three CH₂ groups are optionally replaced by O, S, SO, SO₂, NH or NR⁹ and/or 1–7H atoms are optionally replaced by F and/or Cl, or
A" and A"' together are alternatively an alkylene chain having 2–7 carbon atoms, in which one, two or three CH₂ groups are optionally replaced by O, S, SO, SO₂, NH, NR⁹, NCOR⁹ or NCOOR⁹;
aryl is phenyl, naphthyl, fluorenyl or biphenyl, each of which is unsubstituted or monosubstituted, disubstituted or trisubstituted by Hal, R¹¹, OR¹⁰, N(R¹⁰)₂, NO₂, CN, COOR¹⁰, CON(R¹⁰)₂, NR¹⁰COR¹⁰, NR¹⁰CON(R¹⁰)₂, NR¹⁰SO₂A, COR¹⁰, SO₂N(R¹⁰)₂, or S(O)ₘR¹¹;
R¹⁰ is H or alkyl having 1–6 carbon atoms,
R¹¹ is alkyl having 1–6 carbon atoms,
Het is a monocyclic or bicyclic saturated, unsaturated or aromatic heterocyclic ring having 1 to 2 N, O and/or S atoms, which is unsubstituted or monosubstituted or disubstituted by carbonyl oxygen, Hal, R¹¹, OR¹⁰, N(R¹⁰)₂, NO₂, CN, COOR¹⁰, CON(R¹⁰)₂, NR¹⁰COR¹⁰, NR¹⁰CON(R¹⁰)₂, NR¹⁰SO₂R¹¹, COR¹⁰, SO²NR¹⁰ and/or S(O)ₘR¹¹,
Hal is F, Cl, Br or I, and
m is 0, 1 or 2,
or a pharmaceutically acceptable salt, hydrate, or solvate thereof,
or an isolated stereoisomer or E/Z isomer thereof or mixtures of such stereoisomers or E/Z isomers in all ratios.
2. A compound according to claim 1, in which
R¹, R² are each, independently of one another, alkoxy having 1, 2, 3, 4, 5 or 6 carbon atoms,
or a pharmaceutically acceptable salt, hydrate, or solvate thereof,
or a derivative thereof modified by alkyl, acyl, sugar or oligopeptide groups,
or an isolated stereoisomer or E/Z isomer thereof or mixtures of such stereoisomers or E/Z isomers in all ratios.
3. A compound according to claim 1, in which
R¹, R² are each, independently of one another, H, methoxy, ethoxy, benzyloxy, propoxy, isopropoxy, difluoromethoxy, F, Cl, cyclopentyloxy, cyclohexyloxy or cycloheptyloxy,
or a pharmaceutically acceptable salt, hydrate, or solvate thereof
or an isolated stereoisomer or E/Z isomer thereof or mixtures of such stereoisomers or E/Z isomers in all ratios.

4. A compound according to claim 1, in which
R¹, R² are each, independently of one another, methoxy, ethoxy, propoxy, isopropoxy, cyclopentyloxy or F,
or a pharmaceutically acceptable salt, hydrate, or solvate thereof,
or an isolated stereoisomer or E/Z isomer thereof or mixtures of such stereoisomers or E/Z isomers in all ratios.

5. A compound according to claim 1, in which
R¹ is 4-methoxy,
R² is 3-ethoxy or 3-propoxy,
or a pharmaceutically acceptable salt, hydrate, or solvate thereof,
or an isolated stereoisomer or E/Z isomer thereof or mixtures of such stereoisomers or E/Z isomers in all ratios.

6. A compound according to claim 1, in which
R³ is H, A"R⁷, COA"R⁷, CON(A"R⁷)(A"R⁷) or CO-NR¹⁰-Het,
or a pharmaceutically acceptable salt, hydrate, or solvate thereof,
or an isolated stereoisomer or E/Z isomer thereof or mixtures of such stereoisomers or E/Z isomers in all ratios.

7. A compound according to claim 1, in which
X is methylene, ethylene, propylene or butylene,
or a pharmaceutically acceptable salt, hydrate, or solvate thereof,
or an isolated stereoisomer or E/Z isomer thereof or mixtures of such stereoisomers or E/Z isomers in all ratios.

8. A compound according to claim 1, in which
B is phenyl, pyridyl, pyridyl N-oxide, thienyl, furyl, pyrrolyl, pyridazinyl, pyrimidinyl, pyrazinyl, triazinyl, isoxazolinyl, oxazolinyl, thiazolinyl, pyrazolinyl, imidazolinyl, naphthyl, quinolinyl, isoquinolinyl, cinnolinyl, phthalazinyl, quinazolinyl or quinoxalinyl, each of which is unsubstituted or may be monosubstituted, disubstituted or trisubstituted by R⁴, R⁵ and/or R⁶,
or a pharmaceutically acceptable salt, hydrate, or solvate thereof,
or an isolated stereoisomer or E/Z isomer thereof or mixtures of such stereoisomers or E/Z isomers in all ratios.

9. A compound according to claim 1, in which
B is phenyl, pyridyl, pyridyl N-oxide, thienyl, furyl, pyrrolyl, pyridazinyl, pyrimidinyl, pyrazinyl, triazinyl, isoxazolinyl, oxazolinyl, thiazolinyl, pyrazolinyl, imidazolinyl, naphthyl, quinolinyl, isoquinolinyl, cinnolinyl, phthalazinyl, quinazolinyl or quinoxalinyl, each of which is unsubstituted or may be monosubstituted, disubstituted or trisubstituted by OH, OA, NO₂, NH₂, NAA',

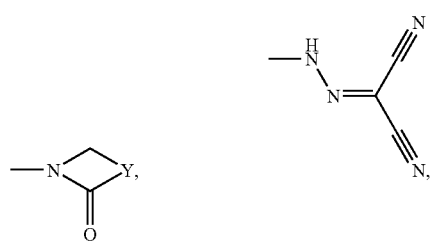

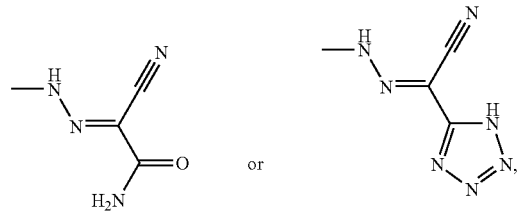

or a pharmaceutically acceptable salt, hydrate, or solvate thereof,
or an isolated stereoisomer or E/Z isomer thereof or mixtures of such stereoisomers or E/Z isomers in all ratios.

10. A compound according to claim 1, in which
B is phenyl which is unsubstituted or monosubstituted by OR¹⁰, NO₂ or

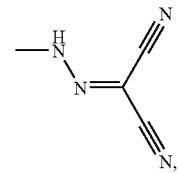

or unsubstituted pyridyl or pyridyl N-oxide,
or a pharmaceutically acceptable salt, hydrate, or solvate thereof,
or an isolated stereoisomer or E/Z isomer thereof or mixtures of such stereoisomers or E/Z isomers in all ratios.

11. A compound according to claim 1, in which
R¹, R² are each, independently of one another, alkoxy having 1, 2, 3, 4, 5 or 6 carbon atoms,
X is methylene, ethylene, propylene or butylene,
R³ is H, A"R⁷, COA"R⁷, CON(A"R⁷)(A"R⁷) or CO-NR¹⁰-Het,
A", A''' are each, independently of one another, a single bond, or alkylene having 1–10 carbon atoms, in which one CH₂ group is optionally replaced by NH or NR⁹, or
A", A''' together are alternatively an alkylene chain having 2–7 carbon atoms, in which one CH₂ group is optionally replaced by NH or NR⁹,
B is phenyl which is unsubstituted or monosubstituted by OR¹⁰, NO₂,

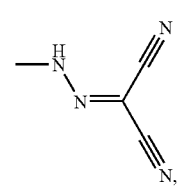

NH₂ or NHCOOA"R⁷, or unsubstituted pyridyl or pyridyl N-oxide,
R⁷ is H, COOH, NHA or NAA',
R⁹ is alkyl having 1–6 carbon atoms,
R¹⁰ is H or alkyl having 1–6 carbon atoms, A, A' are each, independently of one another, alkyl having 1–10 carbon atoms, in which 1–7H atoms are optionally replaced by F and/or Cl, Het is a monocyclic saturated heterocyclic radical having 1 to 2 N atoms, which is optionally monosubstituted or disubstituted by alkyl having 1–6 carbon atoms, or a pharmaceutically acceptable salt, hydrate, or solvate thereof, or an isolated stereoisomer or E/Z isomer thereof or mixtures of such stereoisomers or E/Z isomers in all ratios.

12. A compound according to claim 1, in which $R^1$, $R^2$ are each, independently of one another, alkoxy having 1, 2, 3, 4, 5 or 6 carbon atoms, X is methylene, ethylene, propylene or butylene, $R^3$ is H, A"$R^7$, COA"$R^7$, CON(A"$R^7$)(A'"$R^7$) or CO—N$R^{10}$-Het, A", A'" are each, independently of one another, a single bond or alkylene having 1–10 carbon atoms, in which one $CH_2$ group is optionally replaced by NH or N$R^9$, or A", A'" together are alternatively an alkylene chain having 2–7 carbon atoms, in which one $CH_2$ group is optionally replaced by NH or N$R^9$, B is phenyl which is unsubstituted or monosubstituted by O$R^{10}$, $NO_2$,

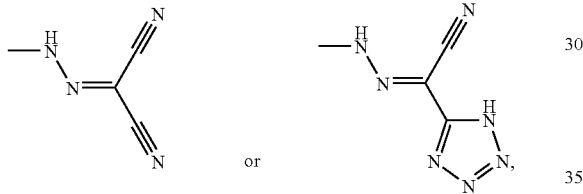

$NH_2$ or NHCOOA"$R^7$, or unsubstituted pyridyl or pyridyl N-oxide, is H, COOH, NHA or NAA', $R^9$ is alkyl having 1–6 carbon atoms, $R^{10}$ is H or alkyl having 1–6 carbon atoms, A, A' are each, independently of one another, alkyl having 1–10 carbon atoms, in which 1–7H atoms may be replaced by F and/or Cl, Het is a monocyclic saturated heterocyclic radical having 1 to 2 N atoms, which is optionally monosubstituted or disubstituted by alkyl having 1–6 carbon atoms, or a pharmaceutically acceptable salt, hydrate, or solvate thereof, or an isolated stereoisomer or E/Z isomer thereof or mixtures of such stereoisomers or E/Z isomers in all ratios.

13. A compound according to claim 1, selected from the group consisting of:

a) 4-methoxybenzaldehyde O-{2-[3-(3-ethoxy-4-methoxyphenyl)-5,6-dihydro-4H-pyridazin-1-yl]-2-oxoethyl}oxime, b) benzaldehyde O-{2-[3-(3-ethoxy-4-methoxyphenyl)-5,6-dihydro-4H-pyridazin-1-yl]-2-oxoethyl}oxime, c) 4-hydroxybenzaldehyde O-{2-[3-(3-ethoxy-4-methoxyphenyl)-5,6-dihydro-4H-pyridazin-1-yl]-2-oxoethyl}oxime, d) pyridine-4-carbaldehyde O-{2-[3-(3-ethoxy-4-methoxyphenyl)-5,6-dihydro-4H-pyridazin-1-yl]-2-oxoethyl}oxime, e) 1-oxypyridine-4-carbaldehyde O-{2-[3-(3-ethoxy-4-methoxyphenyl)-5,6-dihydro-4H-pyridazin-1-yl]-2-oxoethyl}oxime, f) 4-methoxybenzaldehyde O-{2-[3-(4-methoxy-3-propoxyphenyl)-5,6-dihydro-4H-pyridazin-1-yl]-2-oxoethyl}oxime, g) benzaldehyde O-{2-[3-(4-methoxy-3-propoxyphenyl)-5,6-dihydro-4H-pyridazin-1-yl]-2-oxoethyl}oxime, h) pyridine-4-carbaldehyde O-{2-[3-(4-methoxy-3-propoxyphenyl)-5,6-dihydro-4H-pyridazin-1-yl]-2-oxoethyl}oxime, i) 1-oxypyridine-4-carbaldehyde O-{2-[3-(4-methoxy-3-propoxyphenyl)-5,6-dihydro-4H-pyridazin-1-yl]-2-oxoethyl}oxime, j) 4-nitrobenzaldehyde O-{2-[3-(4-methoxy-3-propoxyphenyl)-5,6-dihydro-4H-pyridazin-1-yl]-2-oxoethyl}oxime, k) 4-aminobenzaldehyde O-{2-[3-(4-methoxy-3-propoxyphenyl)-5,6-dihydro-4H-pyridazin-1-yl]-2-oxoethyl}oxime, l) 4-tert-butyloxycarbonylaminobenzaldehyde O-{2-[3-(4-methoxy-3-propoxyphenyl)-5,6-dihydro-4H-pyridazin-1-yl]-2-oxoethyl}oxime, m) 2-{[4-({2-[3-(3-ethoxy-4-methoxyphenyl)-5,6-dihydro-4H-pyridazin-1-yl]-2-oxoethoxyimino}methyl)phenyl]hydrazono}malononitrile, n) 2-{[3-({2-[3-(3-ethoxy-4-methoxyphenyl)-5,6-dihydro-4H-pyridazin-1-yl]-2-oxoethoxyimino}methyl)phenyl]hydrazono}malononitrile, o) 2-{[4-({2-[3-(4-methoxy-3-propoxyphenyl)-5,6-dihydro-4H-pyridazin-1-yl]-2-oxoethoxyimino}methyl)phenyl]hydrazono}malononitrile, p) {2-[3-(3-ethoxy-4-methoxyphenyl)-5,6-dihydro-4H-pyridazin-1-yl]-2-oxoethoxyimino}-2-phenylacetic acid, q) 2-{2-[3-(3-ethoxy-4-methoxyphenyl)-5,6-dihydro-4H-pyridazin-1-yl]-2-oxoethoxyimino}-N-methyl-N-(1-methylpiperidin-4-yl)-2-phenylacetamide, r) 1-(4-methylpiperazin-1-yl)-2-phenylethane-1,2-dione 2-(O-{2-[3-(3-ethoxy-4-methoxyphenyl)-5,6-dihydro-4H-pyridazin-1-yl]-2-oxoethyl}oxime, s) N-(2-dimethylaminoethyl)-2-{2-[3-(3-ethoxy-4-methoxyphenyl)-5,6-dihydro-4H-pyridazin-1-yl]-2-oxoethoxyimino}-2-phenylacetamide, and t) 2-{[4-({2-[3-(3-ethoxy-4-methoxyphenyl)-5,6-dihydro-4H-pyridazin-1-yl]-2-oxoethoxyimino}methyl)phenyl]hydrazono}-2-(1H-tetrazol-5-yl)acetonitrile, or a pharmaceutically acceptable salt, hydrate, or solvate thereof, or an isolated stereoisomer or E/Z isomer thereof or mixtures of such stereoisomers or E/Z isomers in all ratios.

14. A process for making a compound of claim 1, which comprises:

a) reacting a compound of the formula II

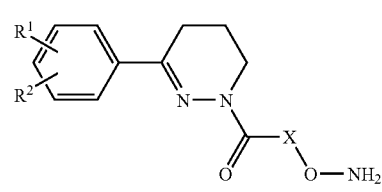

II in which X, $R^1$ and $R^2$ are as defined in claim 1, with a compound of the formula III

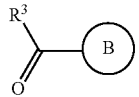
III in which $R^3$ and B are as defined in claim 1, wherein optionally any further OH andlor amino group present is protected by a protecting group and, optionally, the protecting group is subsequently removed, or b) reacting a compound of the formula IV

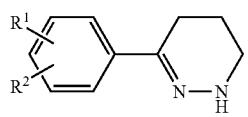
IV in which $R^1$ and $R^2$ are as defined in claim 1, with a compound of the formula V

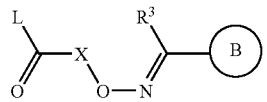
V in which L is Cl, Br, I or a free or reactively functionally modified OH group, and $R^3$, X and B are as defined in claim 1, wherein optionally any further OH and/or amino group present is protected by a protecting group and, optionally, the protecting group is subsequently removed, or c) reacting a compound of the formula VI

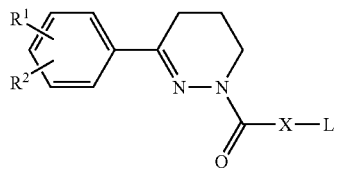
VI in which X, $R^1$ and $R^2$ are as defined in claim 1, and L is Cl, Br, I or a free or reactively functionally modified OH group, with a compound of the formula VII

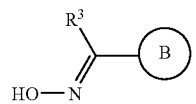
VII in which $R^3$ and B are as defined in claim 1, wherein optionally any further OH and/or amino group present is protected by a protecting group and, optionally, the protecting group is subsequently removed, or d) converting one or more radicals $R^1$, $R^2$, $R^3$ and/or B in a compound of the formula I into one or more other radicals $R^1$, $R^2$, $R^3$ and/or B by i) cleaving an ether or ester,
ii) alkylating or acylating an OH function,
iii) reductively alkylating an amino group,
iv) reacting an amino group with malononitrile,
v) converting a cyano group into a tetrazole group, and, optionally, converting a basic compound of the formula I into a salt thereof by treatment with an acid.

15. A pharmaceutical composition comprising at least one compound of the formula I according to claim 1 or a pharmaceutically acceptable salt, hydrate, or solvate thereof, or an isolated stereoisomer or E/Z isomer thereof or mixtures of such stereoisomers or E/Z isomers in all ratios and a pharmaceutically acceptable excipient.

* * * * *

UNITED STATES PATENT AND TRADEMARK OFFICE
CERTIFICATE OF CORRECTION

PATENT NO. : 7,135,471 B2
APPLICATION NO. : 10/517438
DATED : November 14, 2006
INVENTOR(S) : Hans-Michael Eggenweiler It is certified that error appears in the above-identified patent and that said Letters Patent is hereby corrected as shown below:

Column 59, line 19, reads "CON(A"$R^7$)(A"$R^7$)" should read -- CON(A"$R^7$)(A'''$R^7$), --
Column 59, line 20, reads "N(A"$R^7$)(A"$R^7$)" should read --N(A"$R^7$)(A'''$R^7$), --
Column 59, line 23, reads "andlor" should read -- and/or --
Column 59, line 26, reads "$SO^2$," should read -- $SO_2$, --
Column 59, line 30, reads "$NO^2$," should read -- $NO_2$, --
Column 59, line 33, reads "CON(A"$R^7$)(A"$R^7$)" should read -- CON(A"$R^7$)(A'''$R^7$), --
Column 59, line 55, reads "COGH, COGA," should read -- COOH, COOA, --
Column 59, line 65, reads "CH=CH-" should read -- -CH=CH- --
Column 59, line 65, reads "1-7H atoms" should read -- 1-7 H atoms --
Column 59, line 66, reads "1H atom" should read -- 1 H atom --
Column 60, line 4, reads "1-7H atoms" should read -- 1-7 H atoms --
Column 60, line 9, reads "O,S," should read -- O, S, --
Column 60, line 20, reads "1-7H atoms" should read -- 1-7 H atoms --
Column 60, line 39, reads "$SO^2NR^{10}$" should read -- $SO_2NR^{10}$ --
Column 60, delete lines 53-54, "or a derivative thereof modified by alkyl, acyl, sugar or oligopeptide groups,"
Column 61, line 19, reads "CON(A"$R^7$)(A"$R^7$)" should read -- CON(A"$R^7$)(A'''$R^7$), --
Column 61, line 41, reads "a nd/or" should read -- and/or --
Column 62, line 42, reads "CON(A"$R^7$)(A"$R^7$)" should read -- CON(A"$R^7$)(A'''$R^7$), --
Column 63, line 2, reads "reads "1-7H atoms" should read -- 1-7 H atoms --
Column 63, line 40, reads "is H," should read -- $R^7$ is H, --
Column 63, line 44, reads "1-7H atoms" should read -- 1-7 H atoms --
Column 65, line 13, reads "andlor" should read -- and/or --

Signed and Sealed this

Tenth Day of July, 2007

JON W. DUDAS
*Director of the United States Patent and Trademark Office*